(12) United States Patent
Ziaie et al.

(10) Patent No.: US 9,801,568 B2
(45) Date of Patent: Oct. 31, 2017

(54) GAIT PATTERN ANALYSIS FOR PREDICTING FALLS

(71) Applicant: Purdue Research Foundation, West Lafayette, IN (US)

(72) Inventors: Babak Ziaie, West Lafayette, IN (US); Albert Kim, Lafayette, IN (US); Junyoung Kim, Lafayette, IN (US); Shirley Rietdyk, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/591,561

(22) Filed: Jan. 7, 2015

(65) Prior Publication Data

US 2015/0196231 A1 Jul. 16, 2015

Related U.S. Application Data

(60) Provisional application No. 61/924,434, filed on Jan. 7, 2014.

(51) Int. Cl.
*A61B 5/00* (2006.01)
*A61B 5/11* (2006.01)

(52) U.S. Cl.
CPC .......... *A61B 5/112* (2013.01); *A61B 5/0013* (2013.01); *A61B 5/1117* (2013.01); *A61B 5/1127* (2013.01); *A61B 5/7275* (2013.01); *A61B 5/6831* (2013.01); *A61B 5/6898* (2013.01); *A61B 2576/00* (2013.01)

(58) Field of Classification Search
CPC ......... A61B 5/11; A61B 5/112; A61B 5/1123; A61B 5/1124; A61B 5/1126–5/28
See application file for complete search history.

(56) References Cited

U.S. PATENT DOCUMENTS 4,631,676 A * 12/1986 Pugh .................... A61B 5/1038
348/77
4,813,436 A * 3/1989 Au ........................ A61B 5/1038
356/620

(Continued)

OTHER PUBLICATIONS

Salva, A., et al., Incidence and Consequences of falls among elderly people living in the community. Med Clin (Barc) 2004; 122(5): 172-6.

(Continued)

*Primary Examiner* — Max Hindenburg
(74) *Attorney, Agent, or Firm* — Purdue Research Foundation

(57) ABSTRACT

A method for acquiring gait parameters of an individual is disclosed. The method includes capturing calibration images from foot marker placed on feet or shoes of an individual while an individual is standing still, the calibration images are obtained from a camera worn by the individual, capturing subsequent time-varying images from the foot markers while the individual is walking, and comparing the calibration images to the subsequent time-varying images by a processing unit that is coupled to the camera to determine changes between the initial relative image size of the foot markers and the time-varying images of the foot markers as a function of time to analyze gait of the individual.

15 Claims, 19 Drawing Sheets

(56) References Cited

U.S. PATENT DOCUMENTS

| | | | | |
|---|---|---|---|---|
| 5,800,364 | A * | 9/1998 | Glennie | A61B 5/1074 600/592 |
| 6,231,527 | B1 * | 5/2001 | Sol | A61B 5/1038 348/143 |
| 7,421,369 | B2 * | 9/2008 | Clarkson | A61B 5/061 482/1 |
| 8,269,826 | B2 * | 9/2012 | Nieminen | A61B 5/1121 348/77 |
| 8,698,888 | B2 * | 4/2014 | Bonnet | A61B 5/1114 348/77 |
| 8,718,748 | B2 * | 5/2014 | Reinhold | A61B 5/1113 600/407 |
| 8,961,439 | B2 * | 2/2015 | Yang | A61B 5/1038 600/595 |
| 9,095,251 | B2 * | 8/2015 | Purks | A61B 5/1122 |

OTHER PUBLICATIONS

Maki, B. E., Gait changes older adults: predictors of falls or indicators of fear? J Am Geriatr Soc 1997;45:313-20.

Wild, D., et al., How dangerous are falls in old people at home? Br Med J (Clin Res Ed) 1981;282(6260):266-8.

Reece, A. C., Simpson JM. Preparing older people to cope after a fall. Physiotherapy 1996;82(4):227-35.

Vital Statistics Fourth Quarter and Yearly Summary, 2005. Central Statistics Office: Ireland; 2005, www.cso.ie.

Degen, T., et al. (2003). SPEEDY: A Fall Detector in a Wrist Watch. Proceedings of the Seventh IEEE International Symposium on Wearable Computers (ISWC'03), 2003, 184-187.

Bourke, A. K., et al. "Evaluation of a threshold-based tri-axial accelerometer fall detection algorithm." Gait & Posture, 2007, 26(2): 194-199.

Bourke, A. K. et al., "A threshold-based fall-detection algorithm using a bi-axial gyroscope sensor." Medical engineering & physics, 2008, 30(1): 84-90.

Winter, D. A., et al., Biomechanical walking pattern changes in the fit and healthy elderly. Phys Ther 1990;70: 340-347.

Menz, H. B., et al., Age-related differences in walking stability. Age and Ageing 2003; 32: 137-142.

Hausdorff, J. M., et al. "Gait variability and fall risk in community-living older adults: a 1-year prospective study." Archives of physical medicine and rehabilitation 2001, 82(8): 1050-1056.

Brach, J. S., et al. Too much or too little step width variability is associated with a fall history only in older persons who walk at or near normal gait speed. Journal of NeuroEngineering and Rehabilitation 2005, 2:21, 1-8.

Senden, R., et al., Accelerometry-based gait analysis, an additional objective approach to screen subjects at risk for falling. Gait & Posture, 2012, 36, 296-300.

Moe-Nilssen, R., et al., Interstride trunk acceleration variability but not step width variability can differentiate between fit and frail older adults. Gait & Posture 2005, 21:164-170.

* cited by examiner

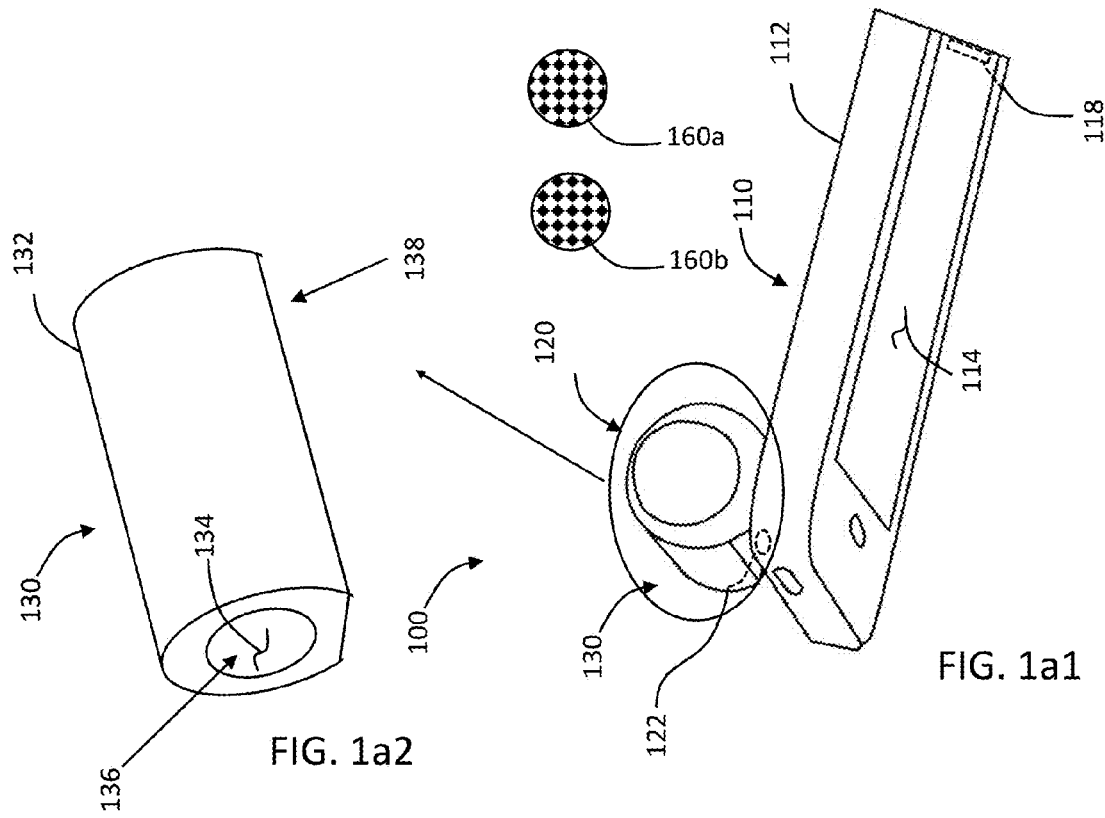
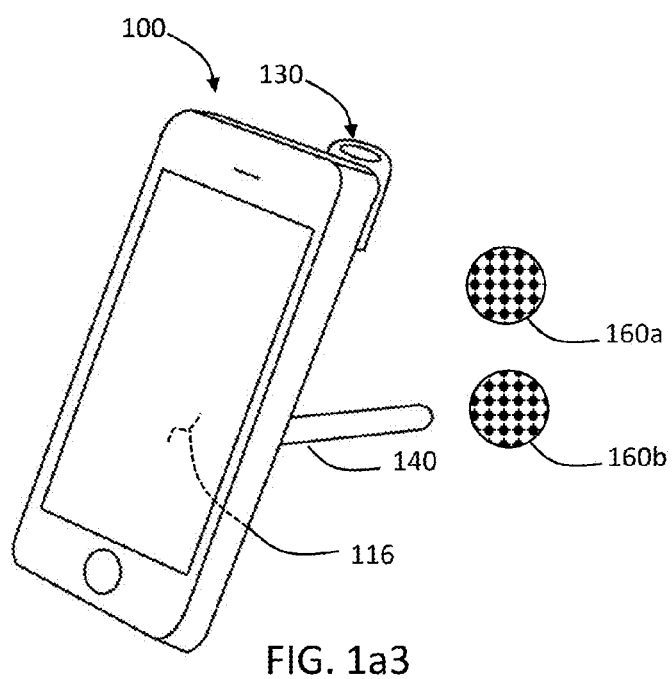
FIG. 1a1
FIG. 1a2
FIG. 1a3

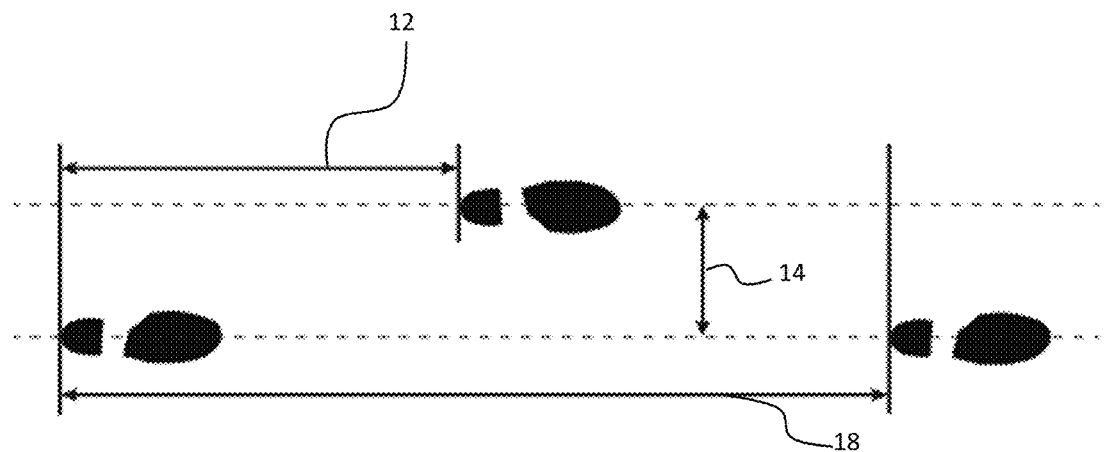
FIG. 1b1
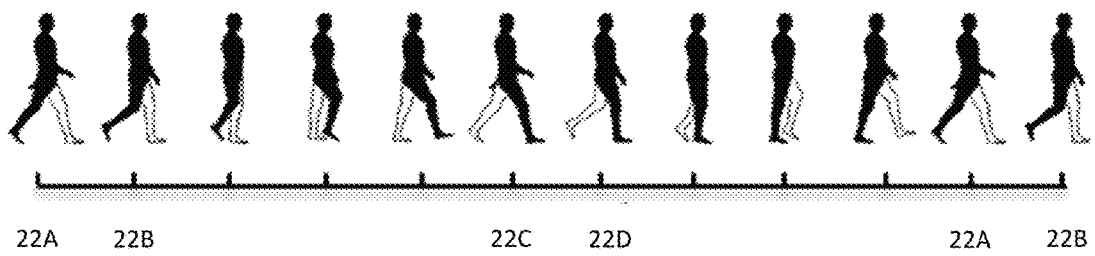
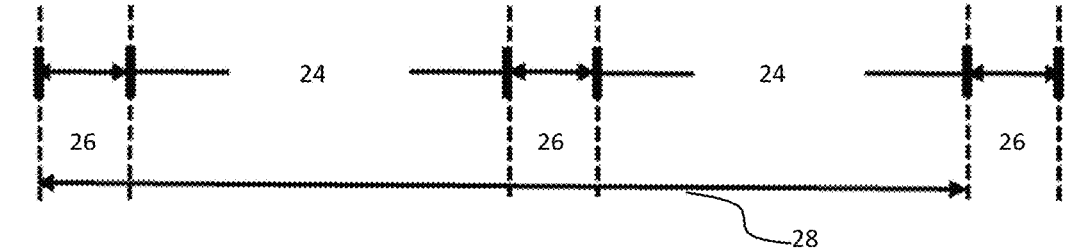
FIG. 1b2

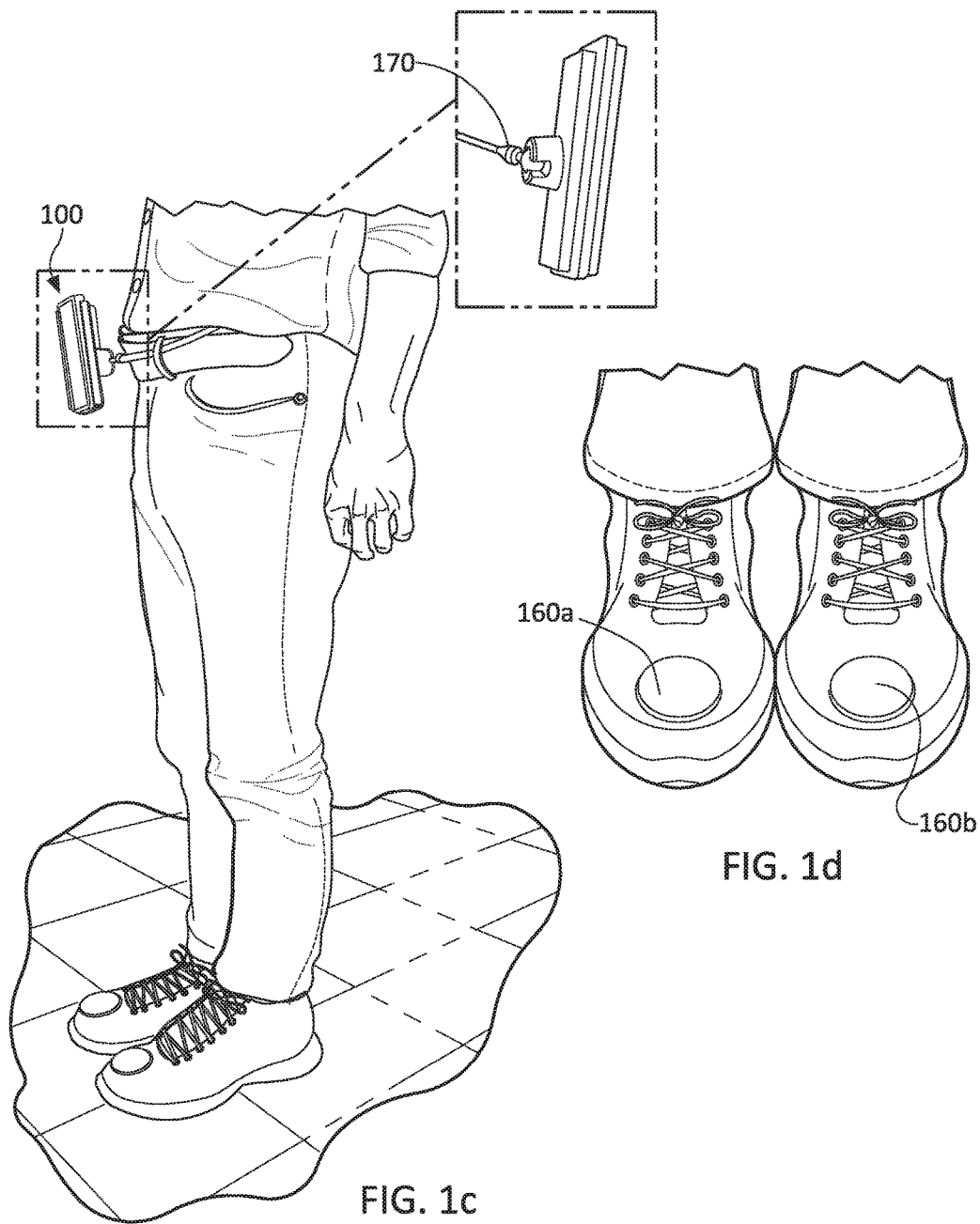

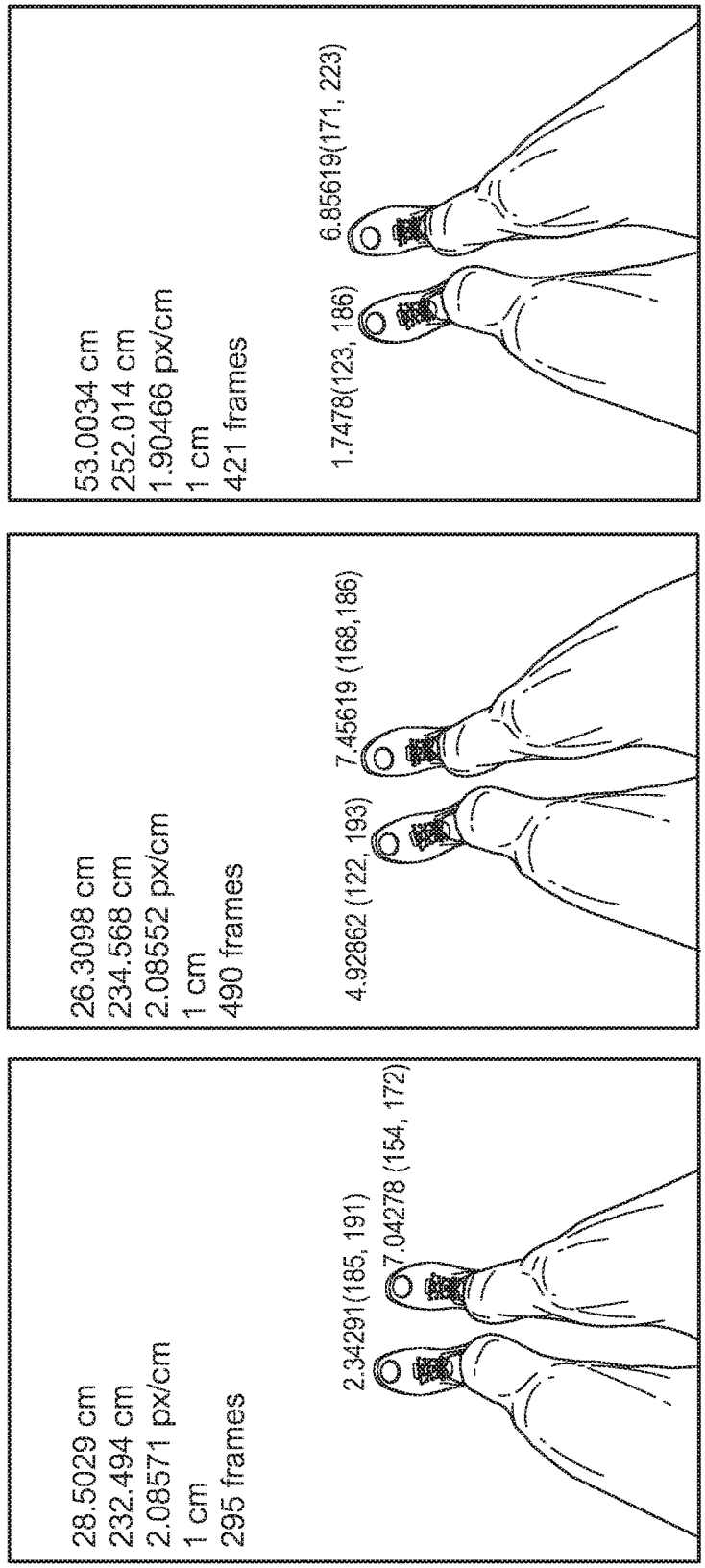
FIG. 1m1  FIG. 1m2  FIG. 1m3

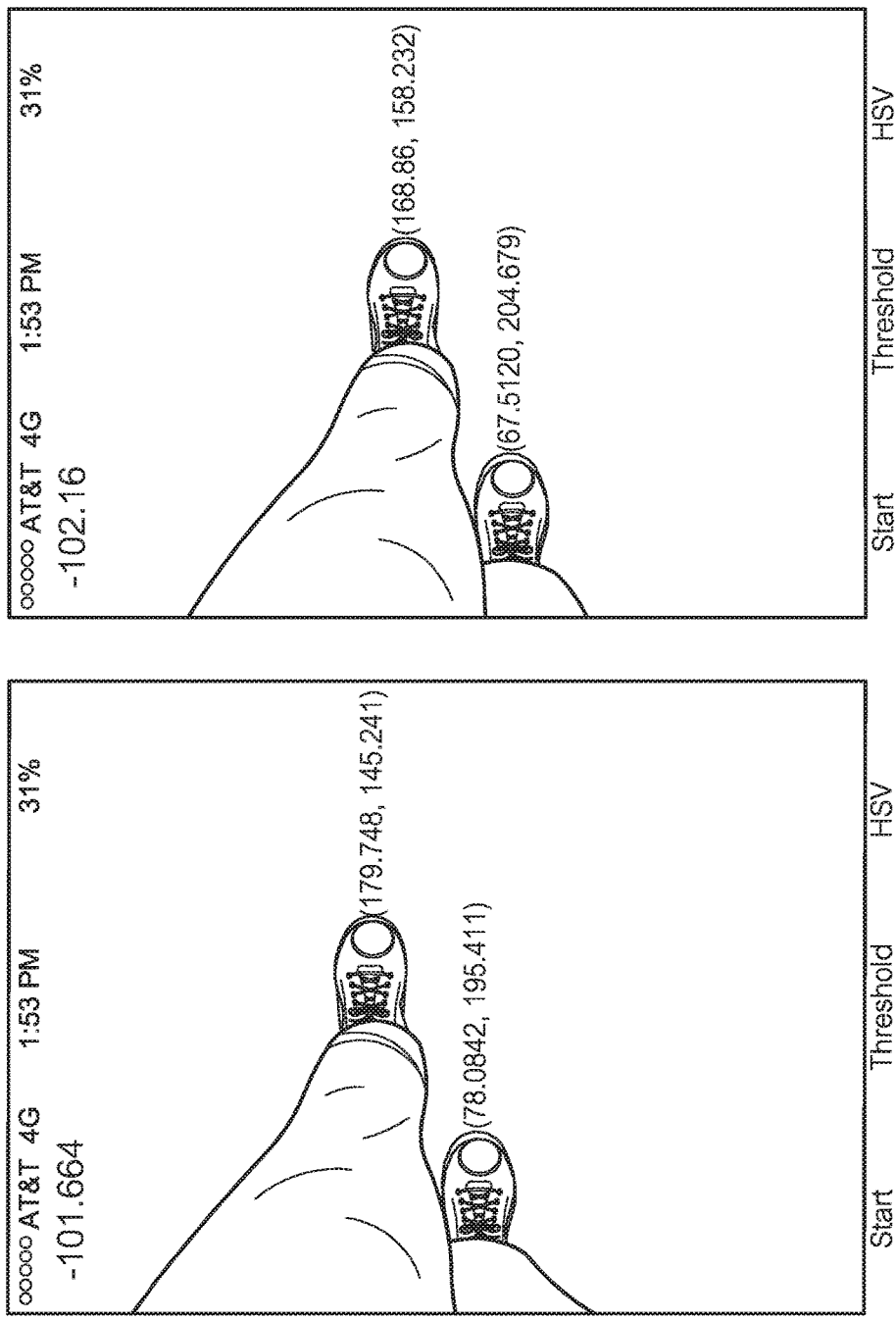

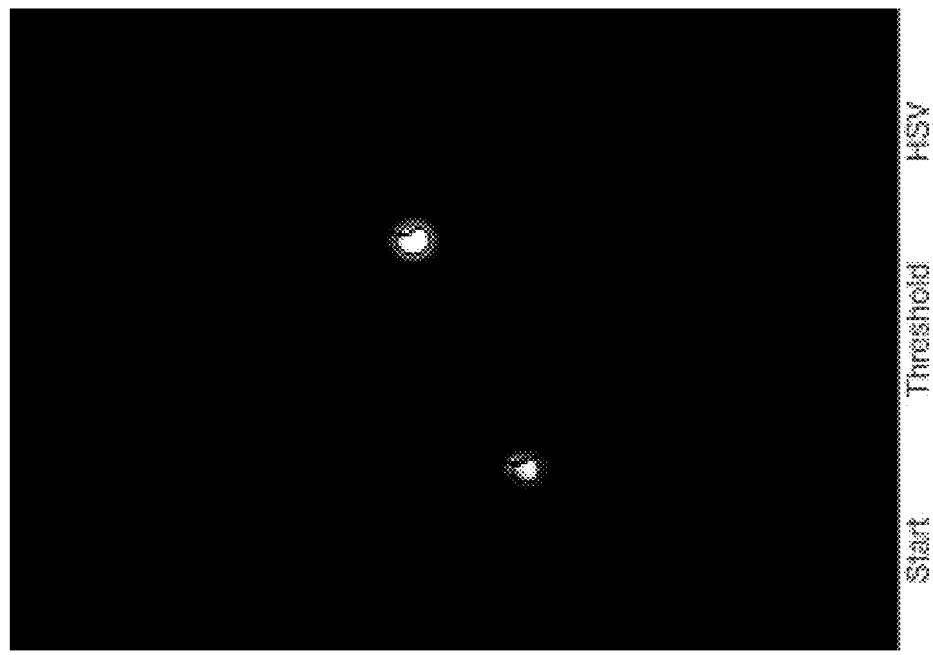
FIG. 3a3

GAIT PATTERN ANALYSIS FOR PREDICTING FALLS

CROSS-REFERENCE TO RELATED APPLICATIONS

The present U.S. patent application is related to and claims the priority benefit of U.S. Provisional Patent Application Ser. No. 61/924,434, filed Jan. 7, 2014, the contents of which is hereby incorporated by reference in its entirety into the present disclosure.

TECHNICAL FIELD

The present disclosure generally relates to a system and methods for collecting, calculating, and outputting data useful in analyzing an individual's gait and predicting falling of an individual.

BACKGROUND

Due to the aging population, falls are a major public health issue. Falls are the leading cause of injury-related death in older adults and falls can lead to chronic pain, disability, loss of independence, and high financial burden. Most falls occur during walking, and gait analyses have been used to predict those who are at greatest risk of falling. Higher risk of falling is associated with slower gait speed, increased stride time variability, increased step length variability, and increased step width variability. It is important to identify those at risk of falling so that professionals can provide interventions. However, these gait measures are not easily obtained; often a comprehensive gait analysis by a physical therapist is required.

Wide-ranging efforts have focused on identifying events that relate to gait and falling. Devices associated with gait and falling can be categorized into two broad categories: (1) fall detection alert systems and (2) analyzing and predicting future falls. The most common approach, the fall detection alert system, is designed to minimize 'long-lie' (i.e., monitoring the length of time a person is unable to get up after a fall) in order to ultimately reduce the amount of medical support the individual receives. However, the most common such system is the push-button method, which cannot be activated if the patient is unconscious. Thus, automated fall detection systems have been developed, including environment-based and wearable detectors. Typical designs involve several sensors. The most accurate devices use environment-based detection, incorporating embedded pressure sensors in the floor and video camera to monitor individuals' movement (Kistler Corp., Winterthur, Switzerland). However, this detection is limited to the instrumented environment and is costly. Wearable detectors, such as watch- or belt-type detectors, are not limited to a specific environment. These detectors often incorporate accelerometers and gyroscopes, monitor the acceleration magnitude and direction, in order detect falls and send an alert to an emergency service. These devices tend to have high false positive rates.

Environment-based and wearable fall detection systems, however, only provide useful data after the fall event, and associated injury, has already occurred. It is especially critical that systems are developed that identify those who are at the greatest risk of falling, so that preventive measures can be implemented and the fall and associated injuries can be avoided. Higher risk of falling is associated with slower gait speed, increased stride time variability, increased step length variability, and altered step width variability (Senden et al. 2012, Hausdorff et al. 2001, Brach et al. 2005, Moe-Nilssen and Helbostad 2005, Maki 1997).

Future fall risk can be predicted by assessing gait, which currently quantified by various tools, including both subjective and objective measures. These measures require a trained therapist, expensive equipment, and time-consuming analyses, so the measures cannot be adopted at a population level. Further, no single test is accepted by clinicians as a reference standard of fall risk. The lack of standard is based on the fact that falls are not caused by a single factor; the causes are multi-factorial, and include issues such as coordination, sensory acuity, cognitive ability, strength, visual ability, medications, and others. Assessment of a single factor or a set of factors is inadequate. However, the effects of these multi-factorial changes are observed in gait parameters, because balanced gait also relies on these factors. Gait analyses, however, are expensive and time-consuming.

Therefore, there is an unmet need for a device that can easily and quickly assess gait parameters. It is important to assess several parameters that have been empirically demonstrated to relate to fall risk: variability of step length, variability of step width, variability of step time, and gait speed. In addition, there is a need for a biofeedback device that will alert the wearer when their gait is compromised; such a device can also be used to provide gait retraining.

SUMMARY

A method for acquiring gait parameters of an individual is disclosed. The method includes capturing calibration images from foot markers placed on feet or shoes of an individual while an individual is standing still, the calibration images are obtained from a camera worn by the individual. The method also includes capturing subsequent time-varying images from the foot markers while the individual is walking. Furthermore, the method includes comparing the calibration images to the subsequent time-varying images by a processing unit that is coupled to the camera to determine changes between the initial relative image size of the foot markers and the time-varying images of the foot markers as a function of time to analyze gait of the individual.

Another method for determining an individual's risk of falling is also disclosed. The method includes gathering real-time gait parameter data from an individual, comparing the gait parameter data to a library of known values, and generating a gait variance to thereby identify an individual's risk of falling.

A smart gait analysis system is also disclosed. The system includes a camera worn by an individual, a processing unit coupled to the camera, a left foot marker placed on the left shoe or foot of the individual, and a right foot marker placed on the right shoe or foot of the individual. The camera is configured to acquire images from the foot markers as the individual is walking. The processing unit is configured to capture calibration images from the foot markers while an individual is standing still obtained from the camera. The processing unit is further configured to capture subsequent time-varying images from the foot markers while the individual is walking. Furthermore, the processing unit is configured to compare the calibration images to the subsequent time-varying images to determine changes between the initial relative image size of the foot markers and the time-varying images of the foot markers as a function of time to analyze gait of the individual.

BRIEF DESCRIPTION OF THE FIGURES

FIG. 1a1 is a perspective view of a gait analysis system according to the present disclosure including an imaging system having a right angle lens assembly and a processing unit.

FIG. 1a2 is perspective view of the right angle lens assembly of FIG. 1a1.

FIG. 1a3 is another perspective view of the gait analysis system according to the present disclosure.

FIG. 1b1 is a timing diagram of human gait cycle showing basic parameters.

FIG. 1b2 is another timing diagram of human gait cycle showing other parameters.

FIG. 1c is a diagram representation of the gait analysis system of the present disclosure worn by a subject with markers (also referred to herein as detectors) on shoes and an imaging system attached to the belt of the subject.

FIG. 1d is a closer diagram representation of the makers of FIG. 1c.

FIGS. 1i1 and 1i2 are alternate patterns for the foot marker in the shape of a cross inside a circle and four smaller circles around a larger circle.

FIGS. 1m1, 1m2, and 1m3 are images of a subject captured by the imaging system of FIG. 1a1.

FIG. 2 is a flow chart depicting steps of one image processing method to be performed on a computer processor, according to the present disclosure.

FIGS. 3a1, 3a2, and 3a3 are images which illustrate the processor processing steps of FIG. 2.

DETAILED DESCRIPTION

Figure 1F:
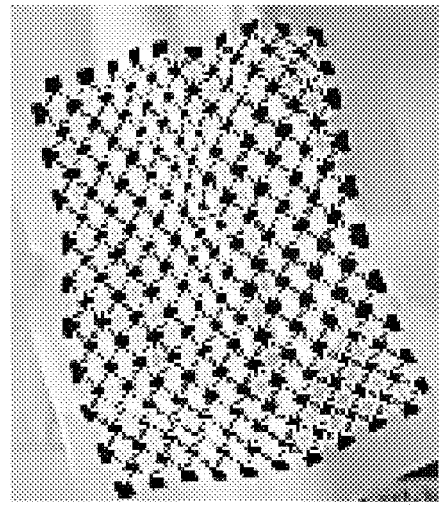
FIGS. 1e, 1f, 1g, and 1h are checkerboard and stripe patterns for foot markers used with the gait analysis system of the present disclosure.
Figure 1H:
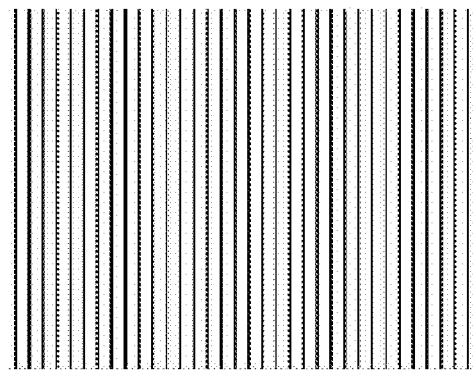
Figure 1E:
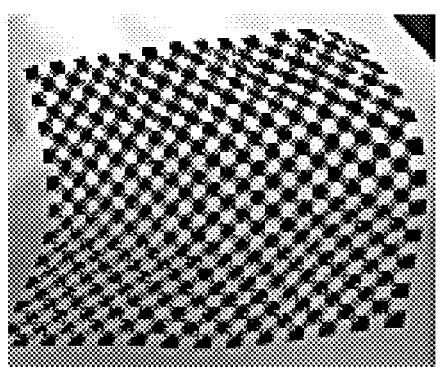
Figure 1G:
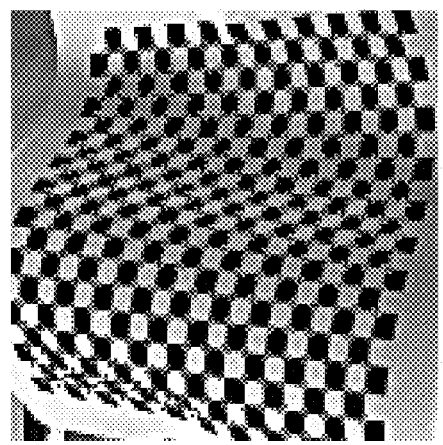
Figure 1J:
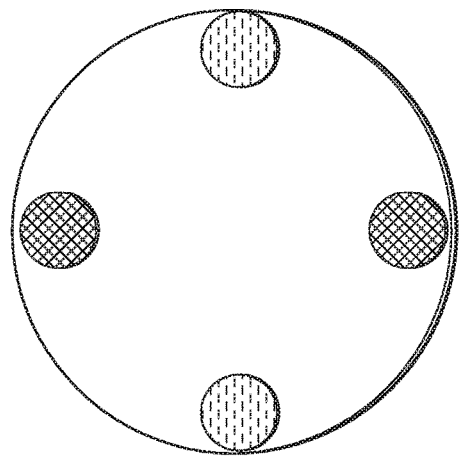
FIG. 1j is a photograph of a subject wearing a marker as well as a light emitting diode on the subject's shoe.
Figure 1J:
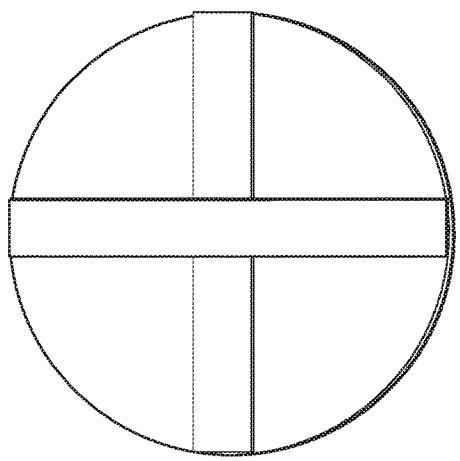
Figure 1J:
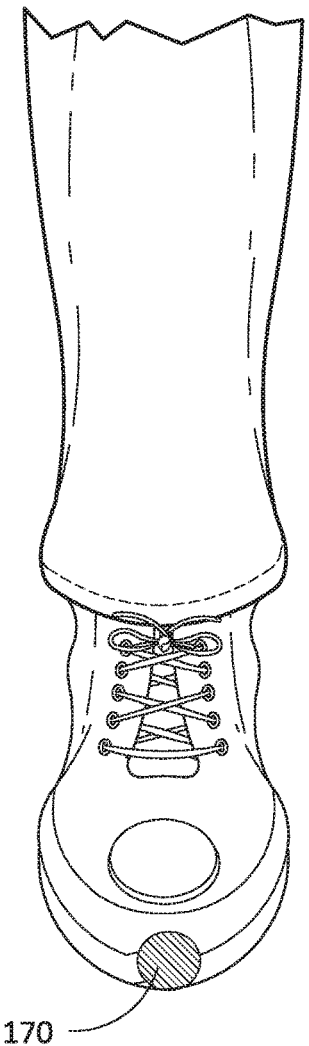

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the need for a more efficient and effective gait analysis and fall detection system, disclosed herein is a novel gait analyzer and fall predictor that can measure step length, step width, step time, step speed, and double support time using an imaging system, processing unit, and a camera feature in a processing unit such as a smart cellular phone.

Figure 2:
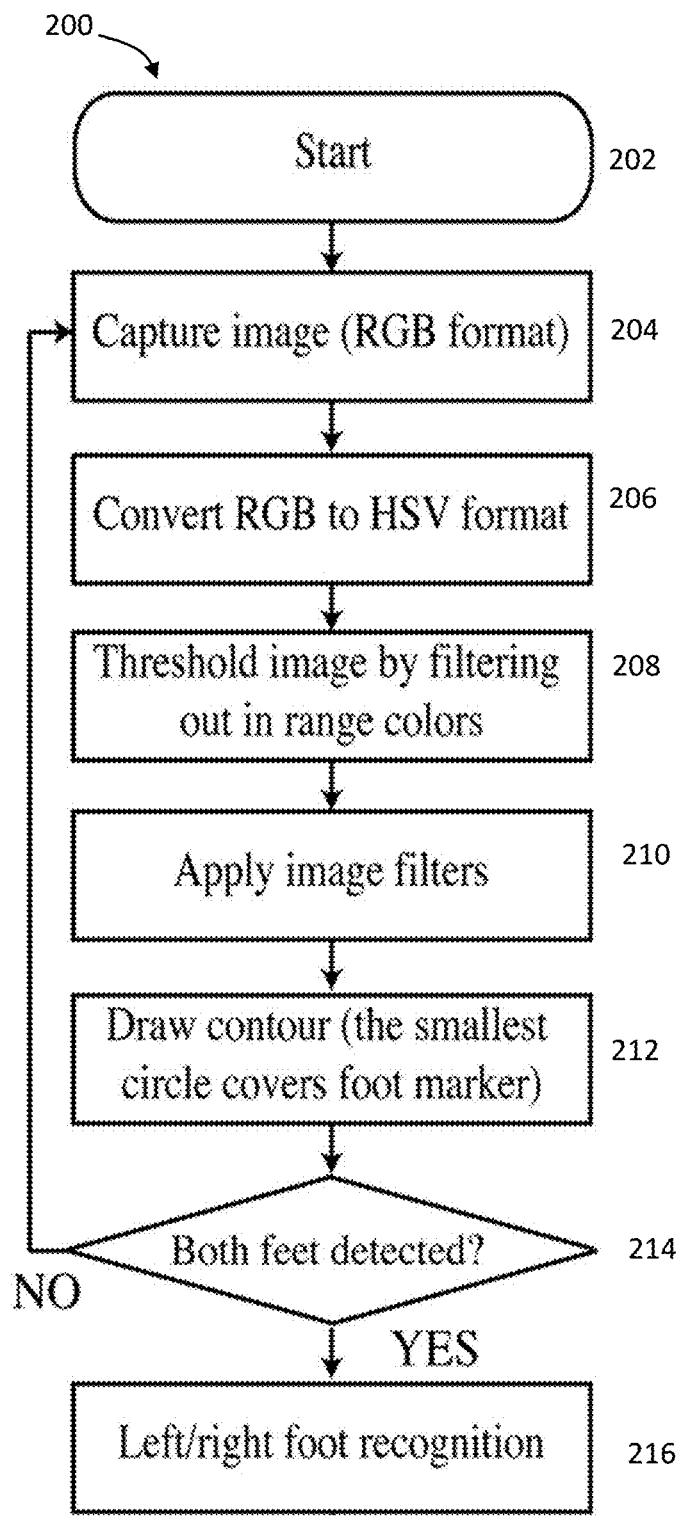
Figure 3B:
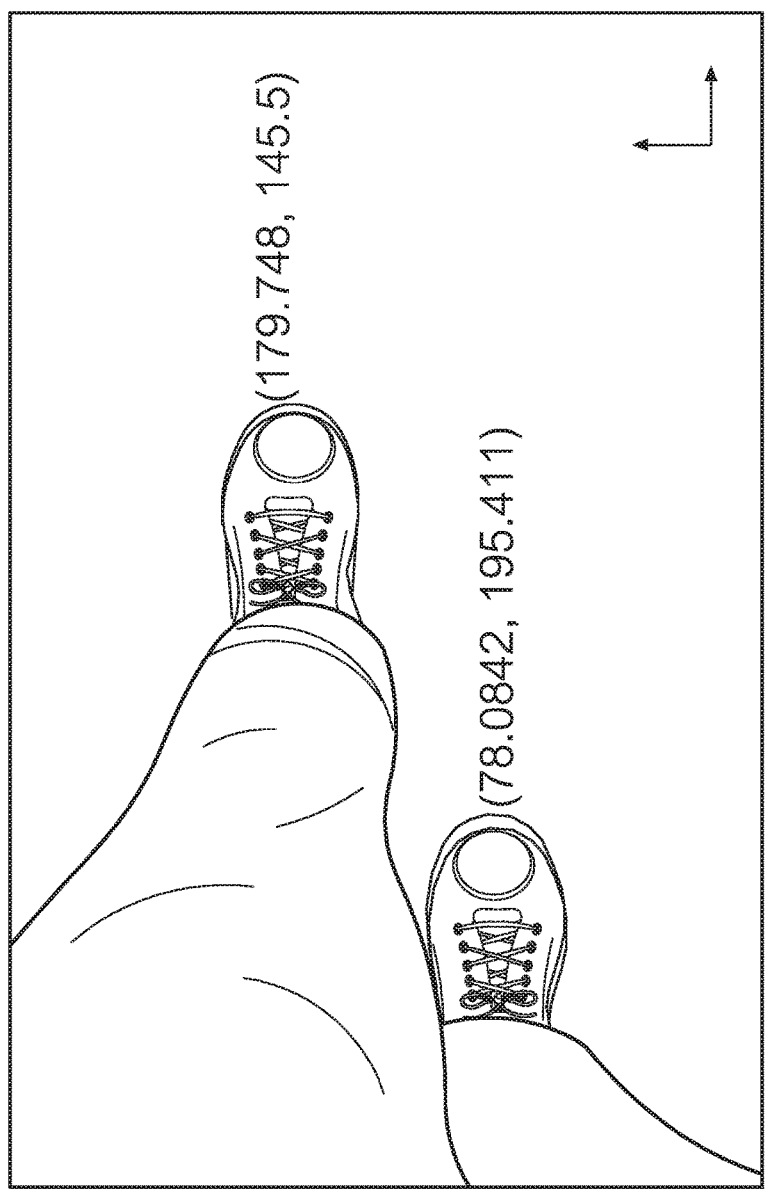
FIG. 3b is an image which illustrates how the location of the foot markers are expressed in a Cartesian coordinate plane with respect to the imaging system coupled to the subject.

Referring to FIGS. 1a2, 1a2, and 1a3, a gait analysis system 100, according to the present disclosure is provided. The gait analysis system 100 generally includes a processing unit 110 and an imaging system 120. The processing unit 110 can be a general purpose processing unit, e.g., a smart cellular phone, such as an APPLE IPHONE, or other processing units, e.g., a special purpose processing unit such as an embedded system paired with an external mountable camera/lens systems. Various embodiments are within the scope of this disclosure. For example, a processing unit may be worn on a subject along with a camera as part of an imaging system capable of obtaining video where the processing unit can process real-time video and any post-processing of data or a separate external processing unit in communications (wireless or wired) with the on-subject processing unit for the purpose of post-processing of data, where the on-subject processing unit is coupled to the camera in a wired or wireless manner; or a wireless or wired camera as part of an imaging system can be worn on the subject while the processing unit(s) is off the subject but in electronic communication (wireless or wired) with the camera. In the latter embodiment, the camera may be configured to communicate image data directly to the processing unit, or indirectly by first recording the image data on a memory device to be used by the processing unit at a later time. Therefore, while the processing unit 110 is shown to be coupled to the imaging system 120, in certain embodiments these units may be only coupled electronically and not physically in contact with each other.

The processing unit 110 is defined by a housing 112, a top surface 114 (including a screen), a bottom surface 116 (FIG. 1a3), and a connector 118. The processing unit 110 includes a processor (not shown) or multiple processors (not shown), memory (not shown), input/output (I/O) circuitry (not shown), and other peripheral circuits typically available in a smart cellular phone. The I/O circuitry may include a wireless communication circuit (not shown), e.g., a Bluetooth system or WiFi, and/or a wired communication circuit (not shown) terminating at the connector 118. The connector 118 is configured to communicate with an external system using a wired communication scheme.

The imaging system 120 includes a camera 122 and optionally a right angle lens assembly 130. It should be noted that the right angle lens assembly 130 may be avoided with the camera 122 placed in a manner in which it is pointed downward toward the shoes/feet of the subject. The camera 122 is typically integrated with the processing unit 110 but can also be part of the right angle lens assembly 130. The right angle lens assembly 130 includes a housing 132 and a lens 134. The lens 134 is positioned at an input side 138 while the camera 122 is positioned at an output side 138. The right angle lens assembly 130 is configured to transfer images from the lens 134 to the camera 122 in a right angle manner. In the embodiment shown in FIGS. 1a1-1s3, the right angle lens assembly 130 is fixedly coupled to the processing unit 110. The processing unit 110 may also optionally be fitted with a belt strap (not shown) and/or a flexible arm holder 140 for coupling the processing unit to a subject's belt.

The right angle lens assembly 130 is configured to tilt the view by 90 degrees and offer a wide angle of view. The camera 122 with the detachable right-angle lens is thus capable of capturing images of a subject's shoes/feet.

To analyze gait of a subject, several parameters need to be monitored. Referring to FIGS. 1b1 and 1b2, some of these parameters are depicted. As a subject walks, it is useful to study steps length 12, step width 14, and stride length 18. The step length 12 is defined as the distance between heel to heel of the left and right feet in the subject's movement. The step width 14 is defined as the distance between the centerlines of each foot as the subject moves. Finally, the stride length 18 is the distance between heel to heel of the same foot as the subject moves.

Referring to FIG. 1b2 additional gait parameters of interest are depicted. FIG. 1b2 is divided into two types of gait, single support 24 and double support 26. In the single support 24, during transition of feet (i.e., at the moment a step is taken), only one foot provides support. Conversely, in the double support 26, both feet provide support. The double support regions are defined by left heel land 22A, and right toe off 22B. The single support regions are defined by right heel land 22C, and left toe off 22D. The transition time between double support 26 to single support 24, back to double support 26, and then back to single support 24 is defined by stride time 28. The gait analysis system 100 of the present disclosure is capable of measuring and analyzing the parameters depicted in FIGS. 1b1, 1b2, speed, and step time. Furthermore, the gait analysis system 100 disclosed herein is capable of measuring step length, step width, step time, gait speed, and variability of all these measures, using a camera that is embedded in many devices.

Referring to FIGS. 1c, and 1d, the gait measurement system 100 is secured to a subject's waist (for example, a belt holster—using the belt strap (not shown), and/or the flexible arm holder 140). Two detachable circular foot markers 160a and 160b (also referred to as detectors herein) are attached to the subject's left and right shoes, respectively.

While the foot markers 160a and 160b may be circular and flat, they may also have a checkerboard pattern, as depicted in FIGS. 1e, 1f, 1g, and 1h. Such designs, when placed on the top of the foot (i.e., placed on the shoe or foot covering the foot's dorsum centered over the proximal phalanges), provides for the measurability of the angle of the foot and thus permits additional data to be acquired about gait analysis (including how the foot lands on and lifts from the ground). In another embodiment, the angle of the foot can be analyzed using lenticular lens principles (not shown) based on using more than one lens and viewing images from each lens and combining the images.

Referring to FIGS. 1i1 and 1i2, according to yet another alternative embodiment, the foot markers incorporate two additional inner strips positioned in a circle or an array of smaller circles positioned at the periphery of a larger circle. In yet another embodiment, referring to FIG. 1j, light emitting diodes (LED) with filter overlays to contour the light to fixed size are placed on the tip of the shoes, allowing the camera 122 to capture the location of the foot markers more easily in low light environments and will thus help to minimize errors in data acquisition. In an alternative embodiment, the LED(s) can be provided around the markers 160a and 160b in a manner in which the two (LEDs and the markers are integrated into one marker assembly (not shown)). In a complementary embodiment, the camera 122 is equipped with infrared (IR) provisions. While green foot markers 160a and 160b were used, it should be noted that other colors can be chosen, noting that solid colors allow for easier detection. Generally, the colors and patterns that produce the highest detection in the widest range of environments are used in the gait analysis system 100.

To yield higher accuracy, a software-based image stabilizer can be implemented. The software-based image stabilizer algorithm uses inertia sensor (i.e., gyroscope sensor and/or accelerometer) information integrated in the processing unit 110. As the subject walks, the subject's waist rotates due to the motion of the lower limbs and pelvis. The software-based image stabilizer compensates the angular movement of subject's waist based on gyroscope sensor information in the XYZ direction, so that the video output is rotated and aligned with the foot markers 160a and 160b. FIGS. 1m1, 1m2, and 1m3 depict results of the software-based stabilizer correction in the gait analysis system 100 where the video output is compensated by the gyroscope sensor.

Figure 4A:
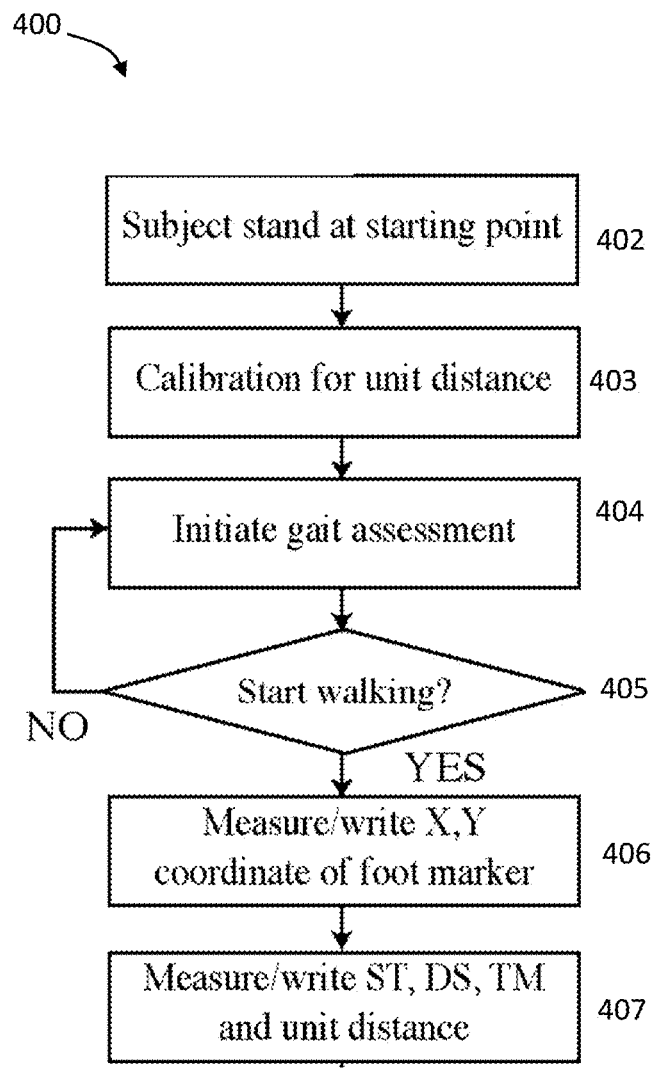
FIG. 4a is a flow chart depicting steps of another and complementary image processing method to be performed on a computer processor, according to the present disclosure.

Referring to FIGS. 2 and 4, general flowcharts 200 and 400 of the gait analysis system 100 are provided, respectively. Referring to FIG. 2, the flowchart 200 starts from the start/stop step 202 where various parameters are initialized, memory purged, or other initialization processes, generally known to a person having ordinary skill in the art. The processing unit 110 captures raw images and/or video at step 204 from the camera 122, which are generally in "Red, Green, Blue" (RGB) format. The RGB format output is then converted to a hue-saturation-value (HSV) image in step 206 to provide more intuitive and perceptual relevance. The foot markers 160a and 160b are then recognized in the HSV image by setting a threshold value for the green color in HSV format (34.85.62~82.255.206). Different foot marker colors can be detected by adjusting parameters in software.

For faster processing, a green circle is used so that when processed it is converted from a green color to a white image and the rest of the images are converted to black in step 208. This output is typically called the "threshold output." For accurate detection of the foot markers, the images need to be filtered. These filters are gray images to maintain intensity information and Gaussian blurs by a Gaussian function to reduce image noise as provided in step 210. Such filters allow for robust detection of foot markers. Once the foot markers 160a and 160b are recognized, the processing unit 110 generates a minimum circle that covers the area of the markers in step 212. In step 214 the flow chart 200 inquires as to whether both circles are detected (referring to both foot markers 160a and 16b). If the answer is no then the flow returns back to step 204, if the answer is yes, then the flow proceeds to step 216, where the location of the foot markers can be expressed in a Cartesian coordinate with respect to the camera 122. Referring to FIGS. 3a1, 3a2, 3a3 and 3b images representing outputs of various steps of the flow chart 200 are provided, once the image processing is complete, Referring further to FIG. 4a, the flowchart 400 begins by a subject first activating the software by establishing the initial position and initialization of other variables according to step 402. Thereafter, the gait analysis system 100 initiates when the subject stands and the foot markers 160a and 160b are recognized by the software (step 402). Once the initialization condition is established, in the calibration step (step 403), a calibration factor (pixels to cm) for the standing positing is established. It should be noted that the calibration factor will change as the distance between the camera and the foot changes during gait (or during climbing steps), and this is included in the data processing (called dynamic calibration of unit distance), performed on the subject-worn processing unit or off-subject processing unit; however, alternatively a single static calibration factor can also be used without taking into account the change in the distance between the camera and feet. The dynamic calibration can be used to generate a pseudo three dimensional gait analysis by not only following the markers 160a and 160b in the XY dimensions (two dimensions), but further follow the position in the third dimension (Z-dimension), by calculating the distance between the camera and the markers 160a and 160b based on the relative size of the markers. Thereafter the calibration method of flow chart 400 continues by ensuring that one foot is being placed ahead of the other foot (that is, the subject begins walking) as provided by step 405. If the method of flow chart 400 does not determine the subject is walking then the flow returns to the initialization step, step 404. If, however, the method determines that subject is moving, then it proceeds to step 406. Because the gait analysis system 100 can detect which foot is the right foot and which foot is the left foot, it can measure the step length and time between steps for one foot with respect to the other. Time and length of steps can be measured continuously at a desired interval. In an experimental setup, the length and time of steps were measured continuously every 1/60 second in which the camera 122 captures sixty frames per second. For every measurement stage, the gait analysis system 100 checks for whether the current stage (n/60 second) length is in increment or decrement when compared to the previous stage ((n−1)/60 second) to identify gait cycle (e.g. single support, double support), as performed in step 406. Note that higher sampling rate yields higher accuracy. Thereafter the step time (ST), Trunk angular motion (TM), DS and unit distance (separation between the camera and foot marker as assessed in the calibration) are measured and written to memory or displayed on the screen of the processing unit for further processing.

Initially the data is optionally not corrected for trunk motion, dynamic calibration of unit distance, and lens distortion as these variables increase demand on the processing unit, which can compromise the sampling rate. However, the trunk motion and marker size parameters can be recorded and used later in a post-processing manner in order to increase the accuracy. Alternatively, more robust processors can be used to perform the same tasks in real-time. Trunk angular motion is assessed with the inertial sensors embedded in the processing unit or separately worn by the subject and communicating with the off-subject processing unit in a wireless or wired manner. The trunk angular motion seen in the frontal (e.g. coronal) plane has the largest effect on image stability since the geometry of the viewing angle changes by the degree of trunk motion. Foot marker size at each frame is also recorded for dynamic calibration in the post-processing (see above). The gait data log (see exemplar log in Table 1) records various parameters, including date, time, sampling frequency, foot number (left foot is 1, right foot is −1, and double support is 0), foot marker size (unit distance), step length (SL), step width (SW), TM, and stride time (ST).

Figure 5A:
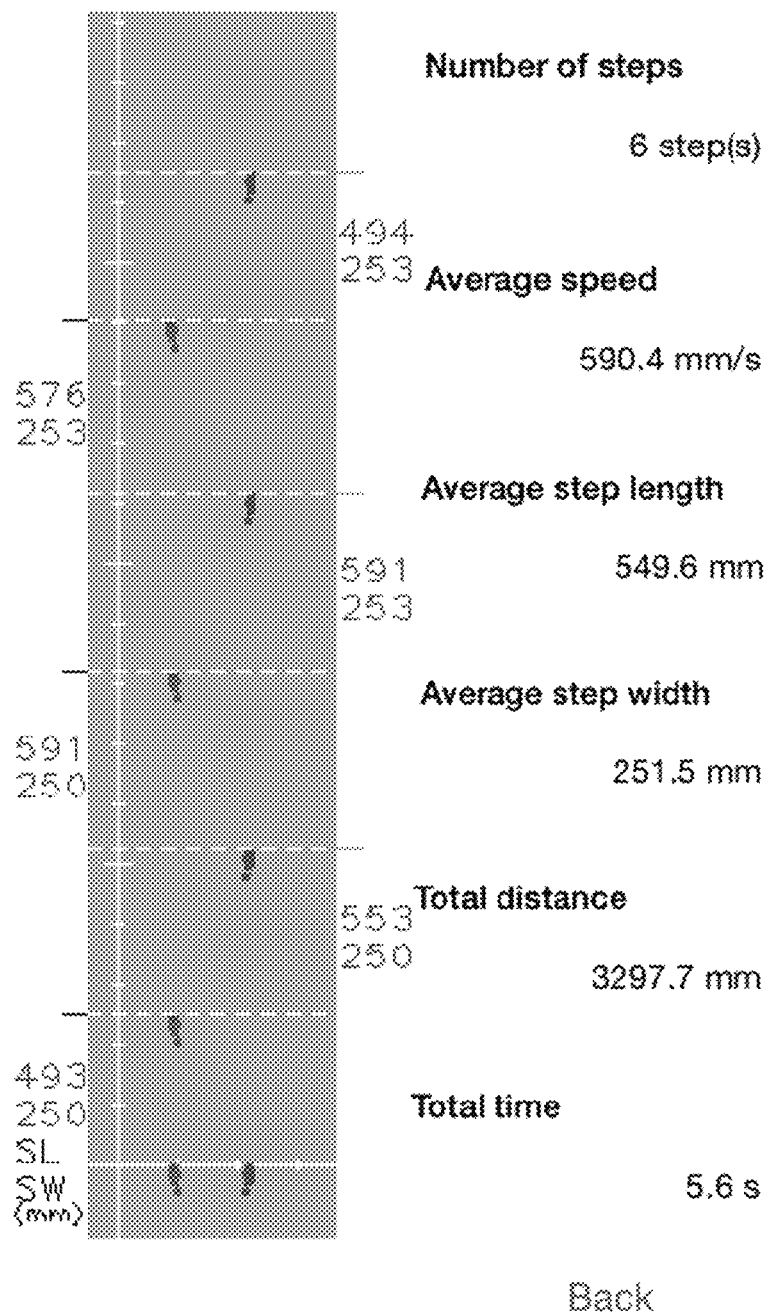
FIG. 5a is a diagram representing a subject's gait provided on a screen by the gait analysis system of the present disclosure.

In the software developed for the system of the present disclosure, gait assessment provides a brief on-screen summary for the users (see example in FIG. 5a). The summaries include, SL and SW for the first 7 to 8 steps (left side of the screen in FIG. 5a) and a report summary of the walking trial, i.e., the number of steps, average gait speed, average step length, average step width, total distance, and the total walking time (right side of the screen in FIG. 5a).

The gait analysis system 100 generates two different data output logs. One is for continuous gait variable data (an example of which is provided in Table 1) and another is a summary of gait variable (an example of which is provided in Table 2). The gait analysis system 100 of the present disclosure has the capability of presenting the gait variable output in two methods in real-time or post processing. When the gait analysis system 100 is connected in a wireless network (e.g., a WiFi or Bluetooth system) to a computer (not shown), the gait variable output data can be displayed on the computer in real-time while the subject walks. Another method to present data output is to store the gait variable output data in the processing unit 110 memory and retrieve the data afterwards for post analysis.

TABLE 1

Example summary of data output log.

| Date | Time | Sampling freq. (FPS) | Foot # | Marker (px) | SL (cm) | SW (cm) | TM (°) | ST (ms) |
|---|---|---|---|---|---|---|---|---|
| 5/7/14 | 13:28:4 | 59.8837 | 1 | 8.62 | 5.1 | 91 | 15.57 | 123.2 |
| . | . | . | . | . | . | . | . | . |
| . | . | . | . | . | . | . | . | . |
| 5/7/14 | 13:34:7 | 59.9535 | 0 | 8.14 | 415.1 | 112.5 | 12.65 | 117 |
| . | . | . | . | . | . | . | . | . |
| . | . | . | . | . | . | . | . | . |
| 5/7/14 | 13:35:5 | 59.9535 | −1 | 8.59 | 440.1 | 96 | 8.31 | 113 |

Figure 4B:
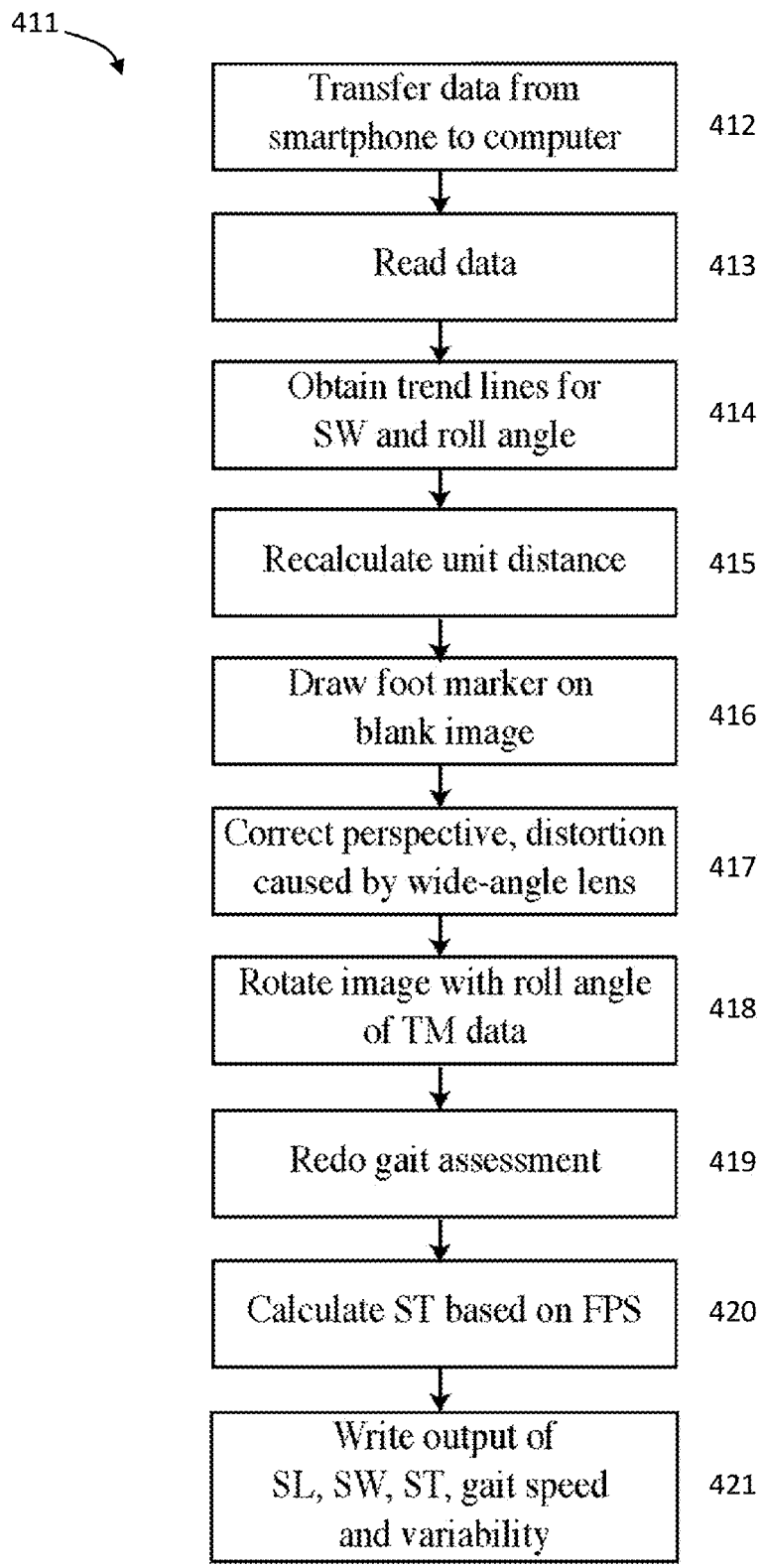
FIG. 4b is a flow chart depicting a post-processing method to increase accuracy by compensating image distortion and trunk motion.

FIG. 4b provides a flow chart 411 for post processing of the gate data. As explained above, by using a robust processor, the post-processing algorithm presented in FIG. 4b can be performed in real-time on the same processing unit. In the post-processing phase, the data from the system of the present disclosure is transferred to a computer (not shown) for further analysis 412, 413. The accuracy of the gait measurement depends primarily on the unit distance, i.e., separation between the camera and foot marker as assessed in the calibration. This distance, however, varies as both the foot and the trunk (i.e., camera) move during gait 414, foot in the Z-direction, and trunk in an angular manner. In the assessment, a single unit distance was calculated in the initial standing calibration to reduce the computational burden. However, in post-processing, dynamic calibration of unit distance is completed by re-calculating from the recorded marker size at each frame 415. Correcting distortion caused by the wide-angle lens will also improve the measurement accuracy as the foot marker usually moves from the bottom edge to the top edge of the screen, where the distortion is greatest 417. The distortion is corrected using the following polynomial model with pre-determined distortion coefficients.

$$x_{corrected}=x+x(1+\lambda_1 r^2+\lambda_2 r^4+\lambda_3 r^6)+[2\rho_1 xy+\rho_2(r^2+2x^2)] \quad \text{(Equ. 1a)}$$

$$y_{corrected}=y+y(1+\lambda_1 r^2+\lambda_2 r^4+\lambda_3 r^6)+[\rho_1(r^2+2x^2)+2\rho_2 xy] \quad \text{(Equ. 1b)}$$

where x, y are coordinates from the input image, $x_{corrected}$, $y_{corrected}$ are corrected coordinates, $\lambda_n$s are radial distortion correcting factors, and $\rho_n$s are tangential distortion correcting factors. To complete the corrections/compensations needed to increase the post-processing accuracy, a marker based on dynamic calibration was drawn on a blank image 416. The intrinsic matrix and distortion coefficients were applied to remove lens distortion 417, then the image was rotated based on measured trunk roll angle 418, followed by a filtering step using and Savitzky-Golay algorithm. Finally, all gait parameters are recalculated 419, 420, and 421.

Double support (DS) time is the time duration when both feet are in contact with the ground between each step (FIG. 1b2). The step length does not change during double support. Double support time begins when the step length reaches its maximum length (end of one step) and continues until the length starts decreasing (start of next step). Referring to Tables 1 and 2, both types of output data logging are provided which include date and time, time elapsed, foot number (right foot number=1, left foot number=−1, and double support foot number=0), step time, step length, step width, and velocity. As shown in FIGS. 1b1 and 1b2, such a numbering system follows gait sequence. For example, if the right foot (foot #=1) started first, time duration is measured until the right foot reaches its maximum step length. Step length for the right foot is measured in centimeters with respect to the left foot. Then, it reaches double support (foot #=0). As soon as gait enters the double support stage, time duration is measured. After double support, the left foot (foot #=−1) starts moving forward and both time and length are measured. Then, gait enters double support (foot #=0) again. In summary, one stride has a sequence of foot number of 1, 0, −1, 0, assuming the right foot started first.

Figure 5B:
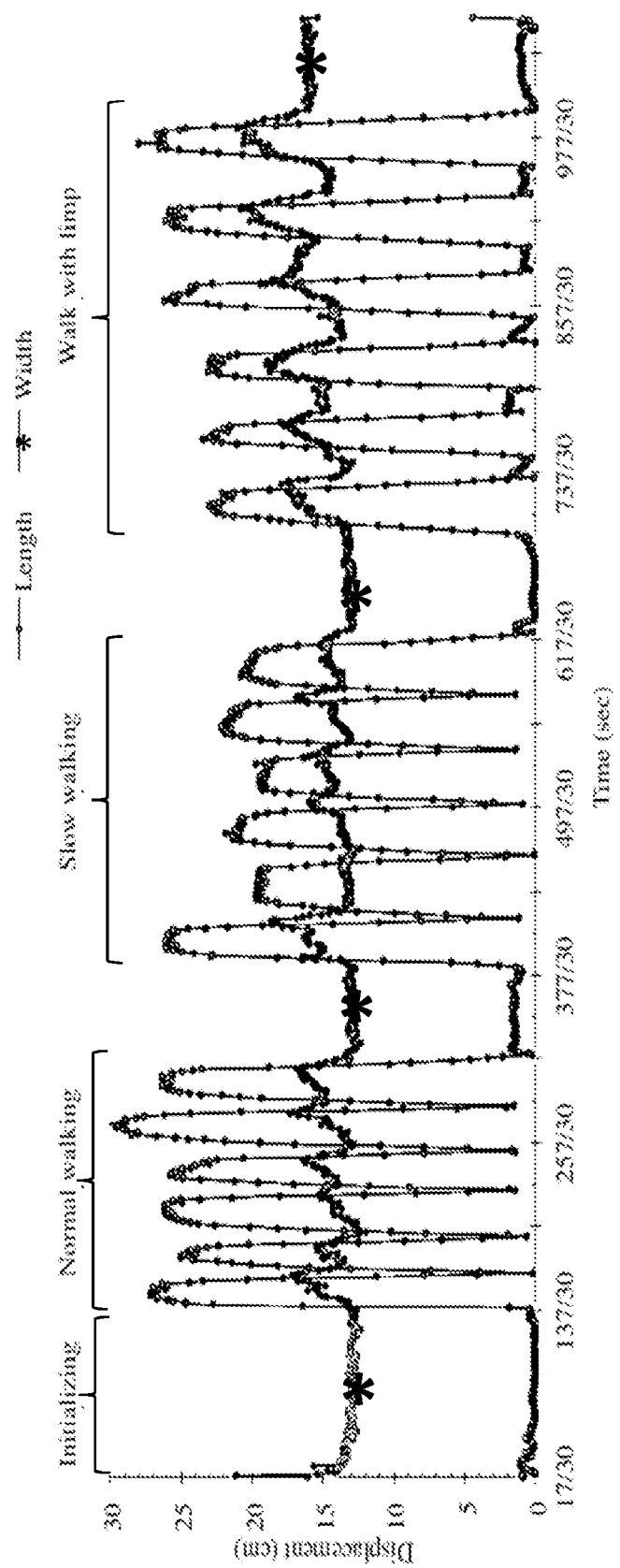
FIG. 5b is a plot of displacement measured in cm vs. time measured in seconds generated by the gait analysis system of the present disclosure in continuous gait with variable speed, depicting the first three strides with normal walking, followed by three strides with slow walking, followed by three strides of limping.
Figure 6:
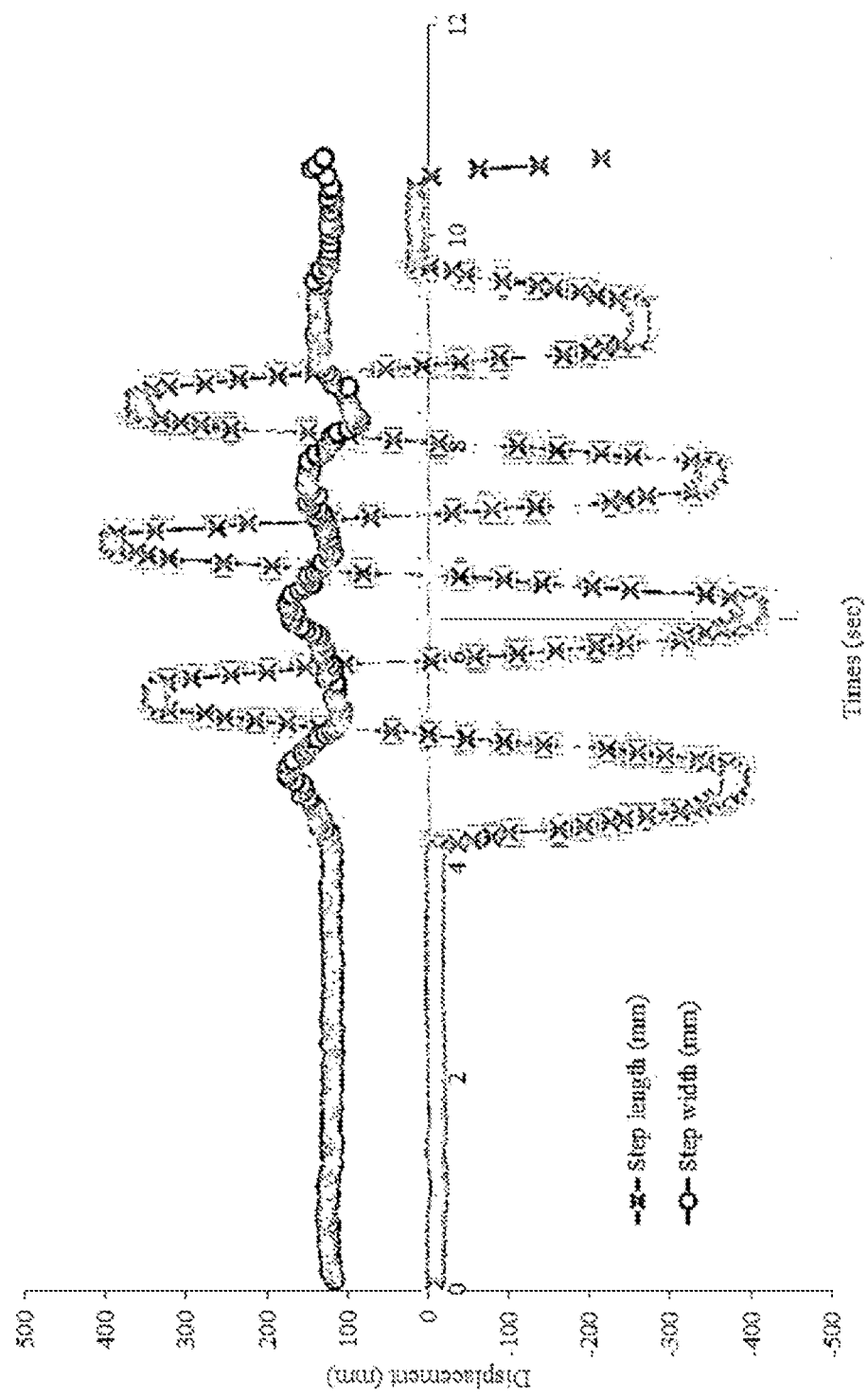
FIG. 6 is a plot of displacement measured in cm vs. time measured in seconds generated by the gait analysis system of the present disclosure with variable speed for interpreting subject's foot movement, where the negative slope represents movement of the left foot and positive slope represents movement of the right foot.

Referring to FIG. 5b, a graph of displacement measured in cm vs. time measured in seconds is provided for one experiment. During the first 4.5 seconds, the method initialized, which includes wearing the apparatus and standing still before actual walking takes place. After initiating (4.5 sec) the subject began to walk. The subject walked with a normal pattern for 6 steps (3 strides). Adding steps by right and left foot indicates one complete stride. FIG. 6 provides another example of graph of displacement measured in cm vs. time measured in seconds is provided for one experiment, where continuous gait data is acquired and provided for the foot markers 160a and 160b versus time. However, FIG. 6 is a slightly different format than FIG. 5b. FIG. 6 depicts the output to distinguish left and right foot more clearly by presenting left foot with negative slope data points and right foot with positive slope data points.

Figure 7:
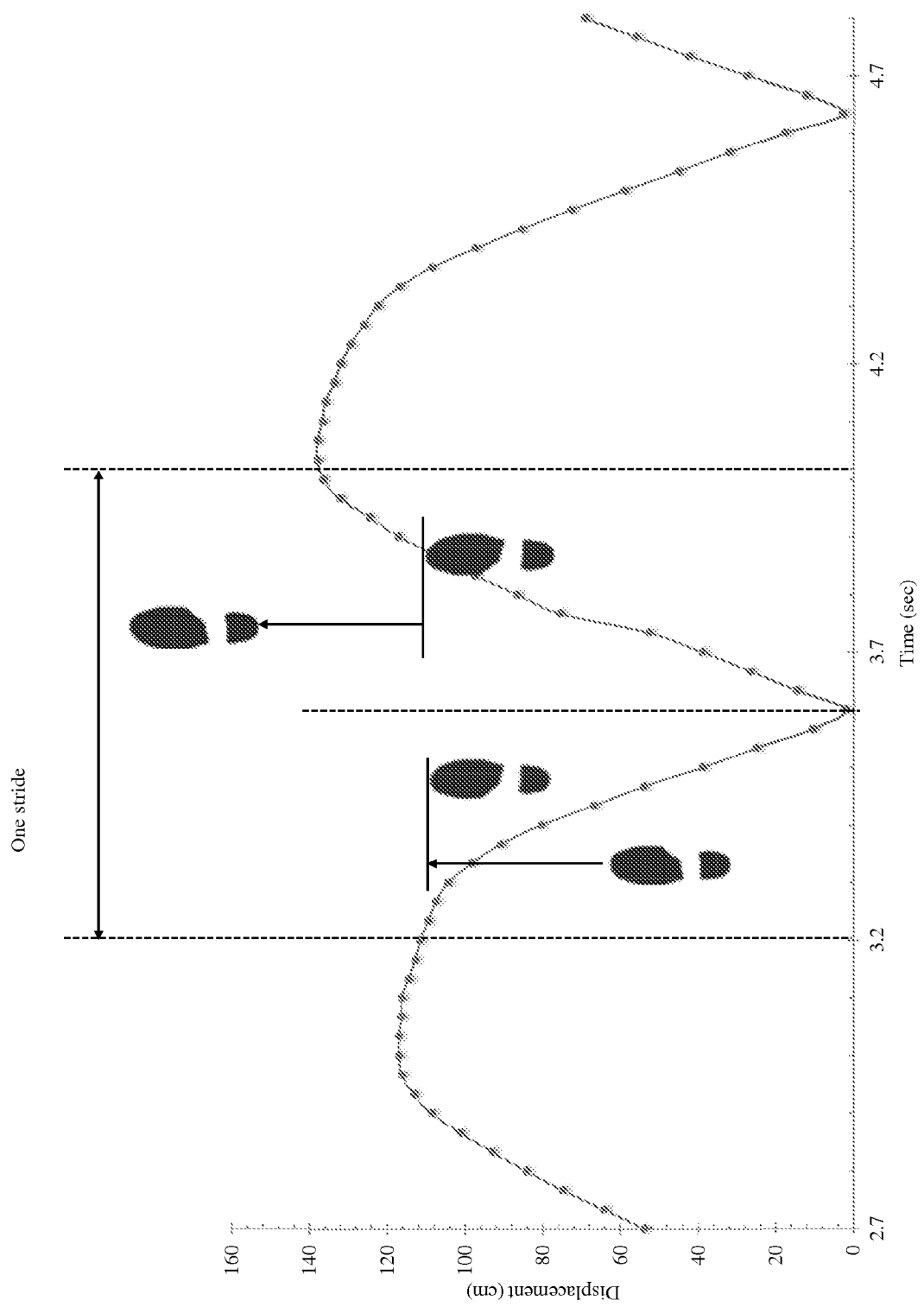
FIG. 7 is a plot of displacement measured in cm vs. time measured in seconds generated by the gait analysis system of the present system which represents one step and stride.
Figure 8:
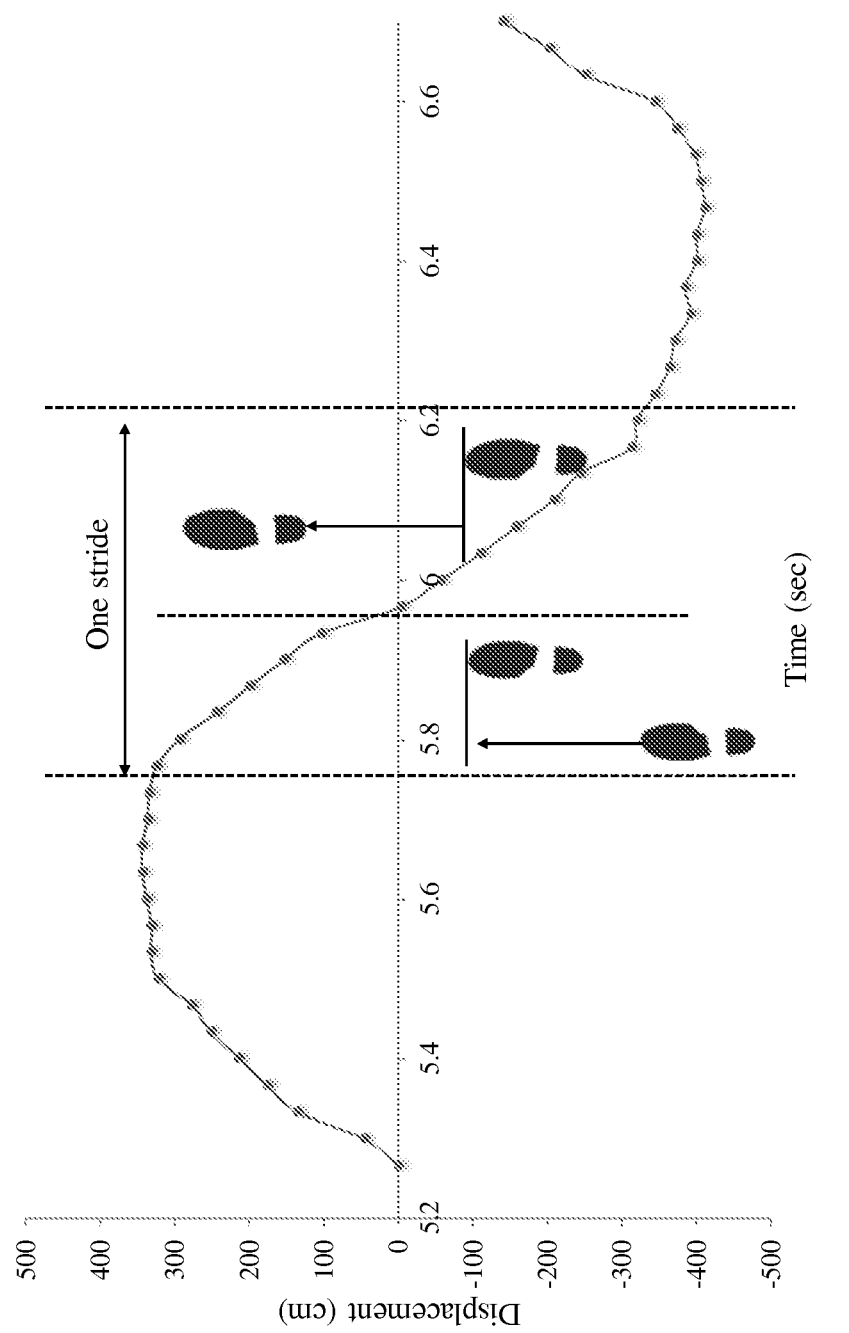
FIG. 8 is a plot of displacement measured in cm vs. time measured in seconds generated by the gait analysis system of the present disclosure which further represents one step and stride.

Referring to FIG. 7 a displacement graph is provided representing one stride of FIG. 5b, while FIG. 8 depicts one stride view of FIG. 6 both of which represent continuous gait analysis output. The displacement is measured from one foot to another. Thus, when a first foot starts moving forward, its length starts decreasing with respect to the second foot. Then, when the first foot passes the second foot, the displacement between the first and second feet becomes zero. The first foot keeps moving forward until it reaches its maximum displacement. During this phase, the displacement with respect to the foot markers 160a and 160b again increases to positive value in FIG. 7 plotting method, while in FIG. 8 plotting method, the displacement increases to negative value. These two methods of plotting can be chosen based on the desired analysis purpose.

From the summary of gait variable data results of first normal walking, the average stride length was 50.95 cm, step width was 15.121 cm, stride time was 0.266 sec, and gait speed was 48.744 cm/sec. The subject then stopped walking for 2 seconds. Then, the subject was asked to walk another 6 steps (3 strides) with slow gait pattern. Average values of a stride length were 38.381 cm, step width was 14.467 cm, stride time was 0.366 sec, and gait speed was 32.07 cm/sec. After another 2 seconds pause, the subject walked with a limp. The subject only used the right foot to move forward. Step length of the right foot was longer compared to the left foot. The average step length was 32.301 cm, step width was 17.611 cm, step time was 0.466 sec, and gait speed was 14.7 cm/sec.

The further validation experiment was performed by direct comparison of the gait analysis system 100 disclosed herein (also referred to as SmartGait) and an optical tracking system (OPTOTRAK), and a pressure-sensing walkway (GAITRITE). Fifteen young healthy adults participated in the study (mean age: 25.8 year, standard deviation: 2.6 years; mean height: 171.1 cm, standard deviation 8.0 cm; mean mass: 70.1 kg, standard deviation 15.6 kg; mean body mass index: 23.8, standard deviation: 4.2). One SmartGait foot marker was placed on each foot dorsum, centered over the proximal phalanges (FIG. 1b). A smartphone was attached to the belt, and adjusted to optimize the field of view. For OPTOTRAK measurements, two infrared emitting diodes (IR LEDs) were placed next to the SmartGait markers. Comparison with OPTOTRAK was used to determine foot movement tracking accuracy of the SmartGait. Comparison with GAITRITE was used to determine gait assessment accuracy, as the foot marker placement for the SmartGait requires different gait parameter calculations than those typically used for gait assessment. Participants were instructed to walk along an 8 m walkway (a 4.3 m GAITRITE was placed in the middle of the walkway) at three different speeds: slow, preferred, and fast speeds. At least 10 trials were collected at each speed, where each trial refers to one pass on the walkway. Within each trial, about 4-7 steps were captured from GAITRITE and SmartGait, and about 2-4 steps from OPTOTRAK (due to 2 m capture volume of OPTOTRAK; the number of steps within each trial changed as a function of gait speed. At the beginning of each trial, the participant initiated the SmartGait software in the smartphone while standing. After the standing calibration was completed by the software (5 s), the participant started walking.

SL, SW, ST, and gait speed were compared between all three systems: SmartGait, OPTOTRAK, and GAITRITE. DS was compared between SmartGait and GAITRITE. The same step was identified in each data collection system in order to directly compare the measures within each step. An average of 155±28 steps was collected per participant. Forty-two percent of the steps were not available for comparison of SmartGait with OPTOTRAK due to the smaller capture volume of the OPTOTRAK. Less than one percent (0.1%) of data was discarded for comparison of SmartGait with the GAITRITE: Occasionally either the GAITRITE or the SmartGait was unable to assess a step. In GAITRITE, this was because the participant stepped off of the sensing area of the pressure-sensing walkway, and in the SmartGait because the thigh obstructed view of at least one of the foot markers during double support phase.

Agreement between the systems was assessed by comparison between the systems for 1) absolute error, 2) absolute error expressed as a percent, 3) intra-class correlation coefficients (ICCs 2, 1) (ICC thresholds were set as poor: <0.40, modest: 0.40-0.74, or excellent: >0.75, and 4) Bland-Altman limits of agreement (LoA). Comparisons were completed on these assessments for SL, SW, ST, gait speed, DS, and its variability within each gait speed. Two sets of comparisons were completed, one for the SmartGait vs. OPTOTRAK and the second for the SmartGait vs. GAITRITE. Absolute error and ICCs were completed for gait analysis, but $LoA$ was only completed for post-processing gait analysis.

The data were also examined to determine how many steps were needed to minimize the error between SmartGait and the criterion systems. The SW difference was calculated as a function of the number of steps included in the average. If the error is random, with enough trials, the error will be minimized. The resulting plot was visually examined to determine when the error did not decrease further, indicting the minimum number of steps needed to minimize the error. All statistical analyses were performed using IBM SPSS Statistics 20 (IBM, Inc.).

As described previously, data from the gait analysis was not corrected for trunk motion, dynamic calibration, or lens distortion. However, it was important to determine if the measurements were adequate for real time feedback. Compare to OPTOTRAK, the average absolute difference in SL and SW between the SmartGait and OPTOTRAK ranged from 1.2 to 8.7 cm with the step length in the fast gait speed condition demonstrating the greatest absolute difference (Table 2a). SL and SW were underestimated relative to the OPTOTRAK. The ICCs indicated excellent concurrent validity for SL, and modest concurrent validity for SW. The absolute error of the calculated step time ranged from 21.1-40.2 ms, with concurrent validity of step time was modest at the fast speed, and excellent at preferred and slow speeds. The SmartGait underestimated the gait speed by 0.11-0.24 m/s, with the underestimation increasing with increasing gait speed (Table 2a). The ICCs for gait speed demonstrated excellent concurrent validity at all assessed speeds. The absolute error of variability between two systems were 0.1-1.2 cm for SL and SW, 8.9-24.9 ms for ST, and 0.01-0.04 m/s for gait speed (Table 2a). However, agreement assessments of variability were modest; average percent error was 11.4% with ICCs ranges from 0.693 to 0.828.

Compare to GAITRITE, the absolute difference between SL and SW calculated from the SmartGait and the GAITRITE ranged 0.1 to 9.6 cm (Table 2b), with the SL in the fastest condition demonstrating the greatest absolute error. The absolute error of step time calculation ranged from 17.9-42.9 ms. The SmartGait underestimated the gait speed by 0.03-0.14 m/s, with the underestimation increasing with increasing gait speed (Table 2b). The ICCs indicated excellent concurrent validity for all assessments at all speeds except for SL at the fast speed, which demonstrated modest concurrent validity. The absolute error of variability were range of 0.1 to 1.1 cm for SL and SW, 4.3 ms to 13.0 ms for ST, and 0.02 to 0.03 m/s for gait speeds. The agreement of variability was modest as average percent error was 10.3% and ICCs range was 0.638 to 0.834.

TABLE 2a

Summary of the SmartGait processing results: SmartGait vs. OPTOTRAK

|  | SmartGait | OPTOTRAK | Abs. error | % error | Var.$_{SmartGait}$ | Var.$_{OPTOTRAK}$ | Abs. var. error | Var. % error | ICC$_{SG-OT}$ | Var. ICC$_{SG-OT}$ |
|---|---|---|---|---|---|---|---|---|---|---|
| Slow speed | | | | | | | | | | |
| Step Length (cm) | 48.1 | 53.2 | 5.1 | 9.6 | 7.9 | 7.5 | 0.4 | 5.5 | 0.823 | 0.802 |
| Step Width (cm) | 12.4 | 15.8 | 3.4 | 21.5 | 4.0 | 4.7 | 0.7 | 15.1 | 0.710 | 0.757 |
| Step Time (ms) | 727.9 | 687.7 | 40.2 | 5.8 | 165.0 | 140.1 | 24.9 | 17.8 | 0.924 | 0.771 |
| Gait Speed (m/s) | 0.70 | 0.81 | 0.11 | 13.6 | 0.23 | 0.22 | 0.01 | 4.5 | 0.882 | 0.754 |
| Preferred speed | | | | | | | | | | |
| Step Length (cm) | 58.3 | 64 | 5.7 | 8.9 | 9.7 | 9.8 | 0.1 | 0.5 | 0.867 | 0.828 |
| Step Width (cm) | 13 | 15.1 | 2.1 | 13.9 | 3.7 | 4.4 | 0.6 | 14.4 | 0.715 | 0.722 |
| Step Time (ms) | 567.1 | 546 | 21.1 | 3.9 | 88.7 | 70.4 | 18.4 | 26.1 | 0.817 | 0.729 |
| Gait Speed (m/s) | 1.07 | 1.2 | 0.13 | 10.8 | 0.27 | 0.26 | 0.01 | 3.8 | 0.856 | 0.693 |
| Fast speed | | | | | | | | | | |
| Step Length (cm) | 65.9 | 74.5 | 8.6 | 11.5 | 11.2 | 12.4 | 1.2 | 9.7 | 0.768 | 0.716 |
| Step Width (cm) | 13.7 | 14.9 | 1.2 | 8.1 | 4.7 | 4.0 | 0.7 | 16.2 | 0.700 | 0.753 |
| Step Time (ms) | 504.2 | 480.7 | 23.5 | 4.9 | 78.7 | 69.7 | 8.9 | 12.8 | 0.706 | 0.713 |
| Gait Speed (m/s) | 1.34 | 1.58 | 0.24 | 15.2 | 0.41 | 0.37 | 0.04 | 10.8 | 0.801 | 0.753 |

TABLE 2b

Summary of the SmartGait processing results: SmartGait vs. GAITRITE

|  | SmartGait | GAITRITE | Abs. error | % error | Var.$_{SmartGait}$ | Var.$_{GAITRITE}$ | Abs. var. error | Var. % error | ICC$_{SG-GR}$ | Var. ICC$_{SG-GR}$ |
|---|---|---|---|---|---|---|---|---|---|---|
| Slow speed | | | | | | | | | | |
| Step Length (cm) | 47.9 | 53.1 | 5.2 | 9.8 | 7.9 | 7.5 | 0.4 | 5.5 | 0.832 | 0.756 |
| Step Width (cm) | 12.4 | 13.8 | 1.4 | 10.1 | 4.3 | 4.0 | 0.2 | 5.4 | 0.822 | 0.761 |
| Step Time (ms) | 734.4 | 777.3 | 42.9 | 5.5 | 170.3 | 157.3 | 13.0 | 8.3 | 0.914 | 0.799 |
| Gait Speed (m/s) | 0.69 | 0.72 | 0.03 | 4.2 | 0.22 | 0.20 | 0.02 | 10.0 | 0.925 | 0.781 |
| Preferred speed | | | | | | | | | | |
| Step Length (cm) | 58.2 | 64.6 | 6.4 | 9.9 | 9.8 | 9.9 | 0.1 | 0.6 | 0.859 | 0.834 |
| Step Width (cm) | 13 | 12.9 | 0.1 | 0.8 | 4.5 | 3.8 | 0.7 | 18.8 | 0.848 | 0.713 |
| Step Time (ms) | 572 | 601.9 | 29.9 | 5.0 | 89.7 | 80.3 | 9.4 | 11.6 | 0.831 | 0.767 |
| Gait Speed (m/s) | 1.06 | 1.1 | 0.04 | 3.6 | 0.29 | 0.26 | 0.03 | 11.5 | 0.878 | 0.725 |
| Fast speed | | | | | | | | | | |
| Step Length (cm) | 66.4 | 76 | 9.6 | 12.6 | 10.8 | 11.7 | 0.9 | 8.0 | 0.731 | 0.638 |
| Step Width (cm) | 13.3 | 12.5 | 0.8 | 6.4 | 4.5 | 3.5 | 1.1 | 30.9 | 0.834 | 0.777 |
| Step Time (ms) | 501.5 | 519.4 | 17.9 | 3.4 | 70.5 | 66.2 | 4.3 | 6.5 | 0.851 | 0.773 |
| Gait Speed (m/s) | 1.36 | 1.5 | 0.14 | 9.3 | 0.33 | 0.35 | 0.02 | 5.7 | 0.873 | 0.766 |

Figure 9A:
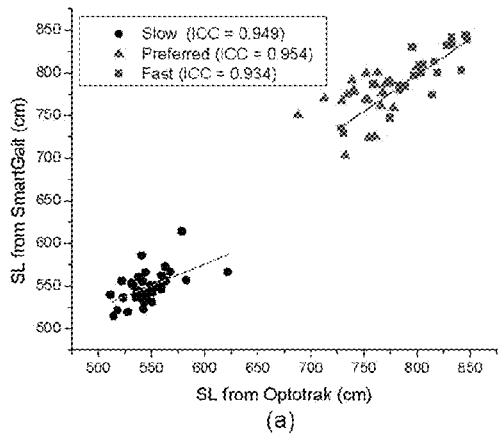
FIGS. 9(a)-9(f) are example graphs of linear regressions for (a and b) step length, (c and d) step width, and (e and f) gait speed from one participant: (a, c, e) OPTOTRAK vs. the system of the present disclosure, (b, d, f) GAITRITE vs. the system of the present disclosure.
Figure 9B:
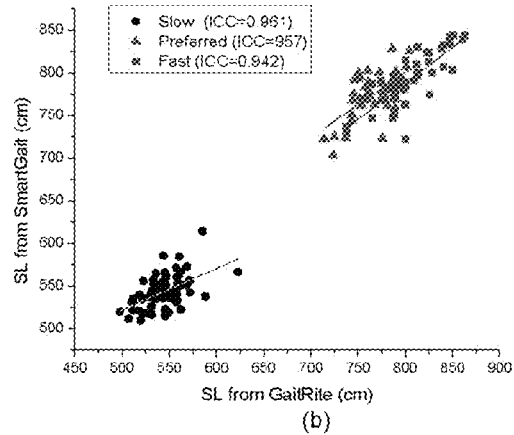
Figure 9C:
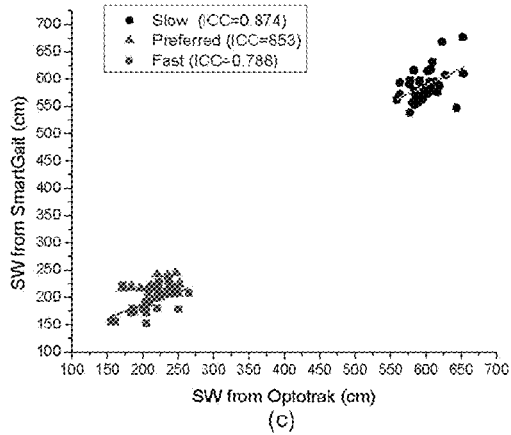
Figure 9D:
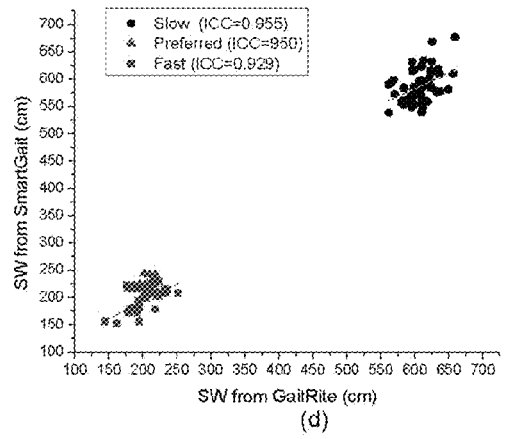
Figure 9E:
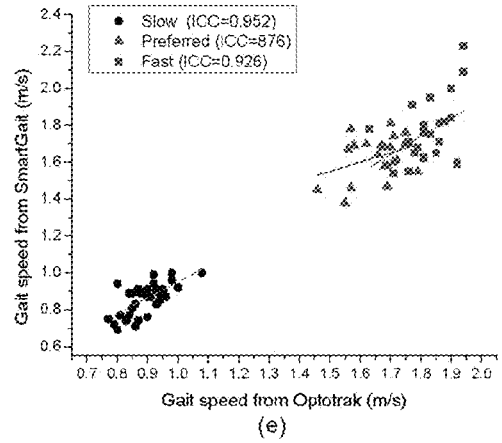
Figure 9F:
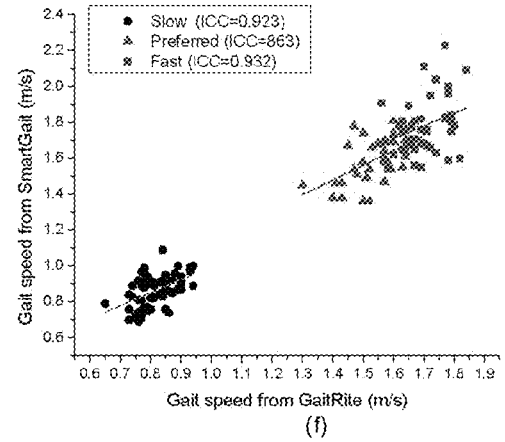

After the image was corrected for trunk motion, dynamic calibration, and lens distortion in the post-processing phase, improvements were observed in almost all measures. The underestimations observed in the processing were no longer present after post-processing. Example data for a single subject indicate the relationship between SL, SW and gait speed obtained from the post-processed data for SmartGait vs. OPTOTRAK (FIGS. 9a, 9c, and 9e) and SmartGait versus GAITRITE (FIGS. 9b, 9d, and 9f).

The ranges of ICC values were 0.700-0.924 and 0.740-0.959, for before and after post-processing, respectively (Tables 2 and 3). Greatest improvements in ICCs were observed for SL, SW and gait speed. Absolute error was reduced by about half for SL and speed, and about one-third for SW, with no improvement in ST. The ICCs indicated excellent concurrent validity for all assessments at all speeds except for ST at the fast speed, which demonstrated modest concurrent validity. The absolute error of variability was 0 to 1.2 cm for SL, 0.3 cm to 0.7 cm for SW, 1.4 to 10.1 ms for ST and 0.01 to 0.04 m/s for gait speed (compared over all gait speeds). The variability agreement was slightly improved in the post-processing as well. The average percent variability error decreased from 11.4% to 6.6% and accordant average variability ICCs improved from 0.749 to 0.835.

The range of ICC values were 0.731-0.925 and 0.831-0.967, for before and after post-processing, respectively (Tables 2 and 3). Greatest improvements in ICC were observed for SL and SW. Absolute error was reduced by about half for SL and SW, with no improvement in ST. The ICCs indicated excellent concurrent validity for all assessments at all speeds. The absolute error of variability was 0.2 to 0.9 cm for SL, 0.1 to 0.2 cm for SW, 0 to 6.1 ms for ST, 0.01 to 0.02 m/s for gait speed and 11.9 to 24.7 ms for DS. The variability ICCs were 0.699 to 0.920 and average variability percent error was 4.3% (or 7.4% with double support time).

TABLE 3a

Summary of the SmartGait post-processing results: SmartGait vs. OPTOTRAK

|  | SmartGait | OPTOTRAK | Abs. error | % error | Var.$_{SmartGait}$ | Var.$_{OPTOTRAK}$ | Var. abs. error | Var. % error | ICC$_{SG-OT}$ | Var. ICC$_{SG-OT}$ |
|---|---|---|---|---|---|---|---|---|---|---|
| Slow speed | | | | | | | | | | |
| Step Length (cm) | 53.3 | 53.2 | 0.1 | 0.2 | 7.4 | 7.5 | 0.0 | 0.1 | 0.949 | 0.819 |
| Step Width (cm) | 13.7 | 15.8 | 2.1 | 13.3 | 4.4 | 4.7 | 0.3 | 6.6 | 0.874 | 0.917 |
| Step Time (ms) | 728.4 | 687.7 | 40.7 | 5.9 | 150.2 | 140.1 | 10.1 | 7.2 | 0.944 | 0.831 |
| Gait Speed (m/s) | 0.77 | 0.81 | 0.04 | 4.9 | 0.21 | 0.22 | 0.01 | 4.5 | 0.959 | 0.841 |
| Preferred speed | | | | | | | | | | |
| Step Length (cm) | 65.3 | 64.0 | 1.3 | 2.0 | 9.8 | 9.8 | 0.1 | 0.6 | 0.954 | 0.867 |
| Step Width (cm) | 13.3 | 15.1 | 1.8 | 11.9 | 4.7 | 4.4 | 0.3 | 6.6 | 0.854 | 0.875 |
| Step Time (ms) | 569.6 | 546.0 | 23.6 | 4.3 | 74.3 | 70.4 | 3.9 | 5.6 | 0.878 | 0.805 |
| Gait Speed (m/s) | 1.18 | 1.2 | 0.02 | 1.7 | 0.31 | 0.27 | 0.04 | 14.8 | 0.957 | 0.848 |
| Fast speed | | | | | | | | | | |
| Step Length (cm) | 74.9 | 74.5 | 0.4 | 0.5 | 13.6 | 12.4 | 1.2 | 9.9 | 0.934 | 0.837 |
| Step Width (cm) | 13.1 | 14.9 | 1.8 | 12.1 | 3.4 | 4.1 | 0.7 | 17.4 | 0.788 | 0.757 |
| Step Time (ms) | 511.5 | 480.7 | 30.8 | 6.4 | 60.1 | 58.7 | 1.4 | 2.4 | 0.74 | 0.797 |
| Gait Speed (m/s) | 1.5 | 1.58 | 0.08 | 5.1 | 0.36 | 0.35 | 0.01 | 2.9 | 0.908 | 0.822 |

TABLE 3b

Summary of the SmartGait post-processing results: SmartGait vs. GAITRITE

|  | SmartGait | GAITRITE | Abs. error | % error | Var.$_{SmartGait}$ | Var.$_{GAITRITE}$ | Var. abs. error | Var. % error | ICC$_{SG-GR}$ | Var. ICC$_{SG-GR}$ |
|---|---|---|---|---|---|---|---|---|---|---|
| Slow speed |  |  |  |  |  |  |  |  |  |  |
| Step Length (cm) | 52.8 | 53.1 | 0.3 | 0.6 | 7.9 | 7.5 | 0.4 | 5.1 | 0.961 | 0.897 |
| Step Width (cm) | 13.7 | 13.8 | 0.1 | 0.7 | 3.9 | 4.0 | 0.2 | 3.7 | 0.955 | 0.778 |
| Step Time (ms) | 734.4 | 777.3 | 42.9 | 5.5 | 163.4 | 157.3 | 6.1 | 3.9 | 0.956 | 0.767 |
| Gait Speed (m/s) | 0.76 | 0.72 | 0.04 | 5.6 | 0.22 | 0.20 | 0.02 | 10.0 | 0.968 | 0.699 |
| Double Support time (ms) | 544.6 | 558.9 | 14.3 | 2.6 | 202.5 | 190.6 | 11.9 | 6.2 | 0.982 | 0.782 |
| Preferred speed |  |  |  |  |  |  |  |  |  |  |
| Step Length (cm) | 65 | 64.6 | 0.4 | 0.6 | 9.7 | 9.9 | 0.2 | 2.1 | 0.967 | 0.920 |
| Step Width (cm) | 13.2 | 12.9 | 0.3 | 2.3 | 3.7 | 3.8 | 0.1 | 2.9 | 0.950 | 0.758 |
| Step Time (ms) | 573.2 | 601.9 | 28.7 | 4.8 | 74.9 | 76.2 | 1.3 | 1.7 | 0.892 | 0.894 |
| Gait Speed (m/s) | 1.17 | 1.10 | 0.07 | 6.4 | 0.28 | 0.26 | 0.02 | 7.7 | 0.951 | 0.860 |
| Double Support time (ms) | 358.8 | 372.4 | 13.6 | 3.7 | 115.4 | 98.5 | 16.9 | 17.1 | 0.925 | 0.824 |
| Fast speed |  |  |  |  |  |  |  |  |  |  |
| Step Length (cm) | 75.7 | 76.0 | 0.3 | 0.4 | 12.6 | 11.7 | 0.9 | 7.5 | 0.942 | 0.710 |
| Step Width (cm) | 12.7 | 12.5 | 0.2 | 1.6 | 3.3 | 3.5 | 0.2 | 4.5 | 0.929 | 0.795 |
| Step Time (ms) | 508.5 | 519.4 | 10.9 | 2.1 | 56.5 | 56.5 | 0.0 | 0.0 | 0.874 | 0.773 |
| Gait Speed (m/s) | 1.52 | 1.50 | 0.05 | 3.3 | 0.35 | 0.34 | 0.01 | 2.9 | 0.934 | 0.776 |
| Double Support time (ms) | 235.7 | 274.9 | 39.2 | 14.3 | 95.0 | 70.3 | 24.7 | 35.1 | 0.807 | 0.745 |

Figures 10A, 10B:
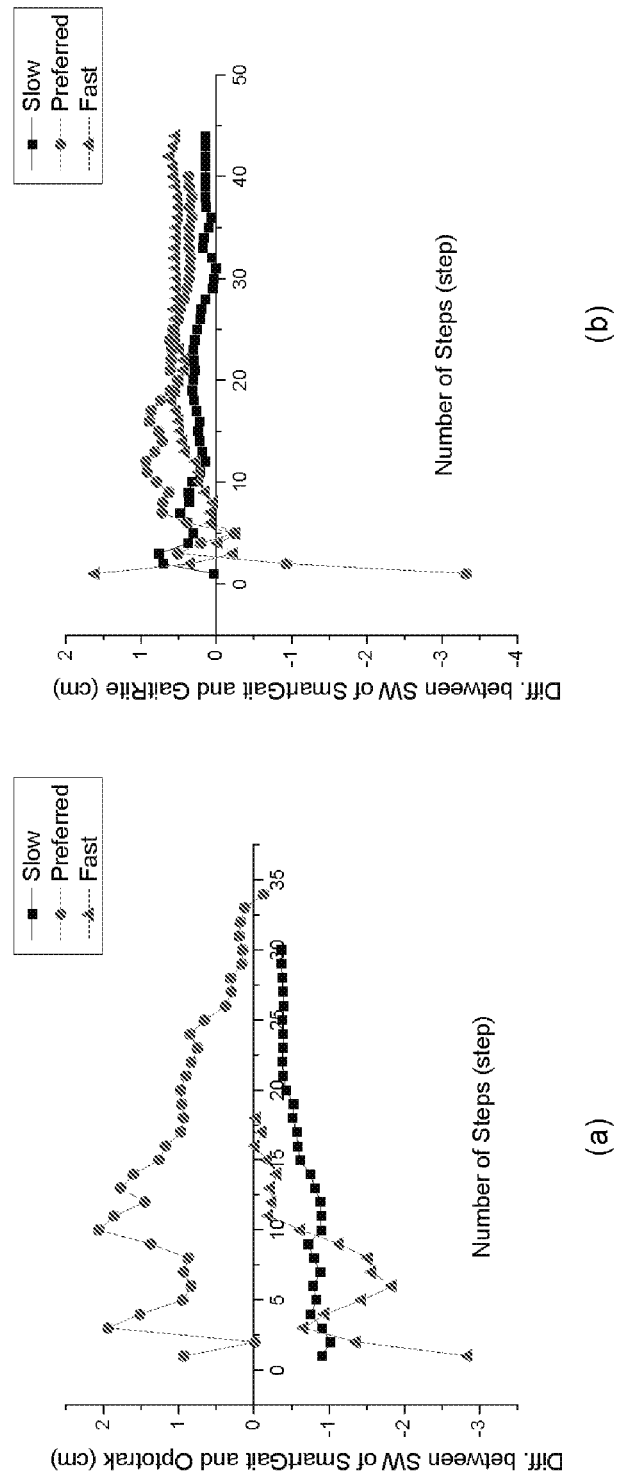
FIGS. 10(a) and 10(b) are graphs of mean of difference between steps between the system of the present disclosure and OPTOTRAK and GAITRITE.

The presence of a bias is likely due to the marker placement for OPTOTRAK versus OPTOTRAK. The SW difference as a function of the number of steps included in the average (FIG. 10) indicated that to reduce the error to 6 mm or less, at least 30 steps are required.

Initial gate assessment data provides gait parameters in real-time, which can be used as biofeedback while the patient is walking. For example, if a patient has been identified with narrow step width, a therapist can enter the ideal value for step width into the SmartGait. When the patient walks, SmartGait will calculate and compare step width to the threshold. When the SW is too narrow (relative to the threshold), a visual, auditory, or vibratory, or other types of biofeedback cued will remind the subject to widen their step. Thus, SmartGait has the ability to provide real-time biofeedback on each step and will allow the patient to self-correct their gait. The average gait information can also be processed to quantify overall performance from day to day for further diagnosis and intervention by the therapist. However, it is important to note that the error in individual steps is ±3.3 cm in pilot study (TABLE 3). Therefore, the threshold must account for this error. For example, if the goal is a 15 cm SW, the threshold for feedback should be 11.5 cm (15-3.5 cm). Therefore, whenever SmartGait detects 11.5 cm or narrower SW, a cue would be provided.

The gait data that is acquired from gait analysis system 100 of the present disclosure can be used to predict falls, as there is a known association between gait variables and fall risk. The data acquired by the gait analysis system 100 can be stored and compared to a library of known parameters associated with fall risks. The individual's values will be compared to these libraries to determine if any of the parameters exceed the threshold. If the threshold is exceeded on one or more parameters, the individual will be identified as being at higher fall risk.

Those skilled in the art will recognize that numerous modifications can be made to the specific implementations described above. The implementations should not be limited to the particular limitations described. Other implementations may be possible. While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for acquiring gait parameters of an individual, comprising:
   capturing calibration images from foot markers placed on feet or shoes of an individual while an individual is standing still, the calibration images are obtained from a camera worn by the individual;
   capturing subsequent time-varying images from the foot markers while the individual is walking; and
   comparing the calibration images to the subsequent time-varying images by a processing unit that is coupled to the camera to determine changes between the initial relative image size of the foot markers and the time-varying images of the foot markers as a function of time to analyze gait of the individual.

2. The method of claim 1, the camera is an integral part of the processing unit.

3. The method of claim 1, the camera physically coupled to the processing unit.

4. The method of claim 1, the camera electronically coupled to the processing unit.

5. The method of claim 4, the coupling is by a wireless channel.

6. The method of claim 1, each of the foot markers includes at least one identifiable feature such that the foot marker can be identified in the images.

7. The method of claim 6, the identifiable feature is a color.

8. The method of claim 7, the color is a solid color.

9. The method of claim 6, the identifiable feature is a pattern.

10. The method of claim 9, the pattern is a checker pattern.

11. A smart gait analysis system, comprising:
a camera worn by an individual;
a processing unit coupled to the camera;
a left foot marker placed on the left shoe or foot of the individual; and
a right foot marker placed on the right shoe or foot of the individual,
the camera is configured to acquire images from the foot markers as the individual is walking,
the processing unit is configured to
capture calibration images from the foot marker while an individual is standing still obtained from the camera,
capture subsequent time-varying images from the foot markers while the individual is walking, and
compare the calibration images to the subsequent time-varying images to determine changes between the initial relative image size of the foot markers and the time-varying images of the foot markers as a function of time to analyze gait of the individual.

12. The gait analysis system of claim 11, the camera is an integral part of the processing unit.

13. The gait analysis system of claim 11, the camera physically coupled to the processing unit.

14. The gait analysis system of claim 11, the camera electronically coupled to the processing unit.

15. The gait analysis system of claim 14, the coupling is by a wireless channel.

* * * * *